(12) United States Patent
Bystrom et al.

(10) Patent No.: US 8,362,417 B2
(45) Date of Patent: Jan. 29, 2013

(54) MASS SPECTROMETRY ASSAY FOR PLASMA-RENIN

(75) Inventors: Cory E. Bystrom, Ladera Ranch, CA (US); Richard E. Reitz, San Clemente, CA (US); Nigel J. Clarke, Oceanside, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 13/330,537

(22) Filed: Dec. 19, 2011

(65) Prior Publication Data

US 2012/0088260 A1 Apr. 12, 2012

Related U.S. Application Data

(63) Continuation of application No. 12/715,343, filed as application No. PCT/US2009/053189 on Aug. 7, 2009, now Pat. No. 8,106,351, and a continuation-in-part of application No. 12/189,092, filed on Aug. 8, 2008, now Pat. No. 7,834,313.

(51) Int. Cl.
    *H01J 49/26* (2006.01)
(52) U.S. Cl. ............... 250/282; 250/288; 435/23
(58) Field of Classification Search ........... 250/282, 250/288; 435/23, 23.2, 226, 325
    See application file for complete search history.

(56) References Cited

U.S. PATENT DOCUMENTS

| | | | |
|---|---|---|---|
| 3,984,532 A | 10/1976 | Fernandez de Castro | |
| 4,022,577 A | 5/1977 | Brooker et al. | |
| 4,112,064 A | 9/1978 | Farrenkopf et al. | |
| 5,572,025 A | 11/1996 | Cotter et al. | |
| 5,869,832 A | 2/1999 | Wang et al. | |
| 6,107,623 A | 8/2000 | Bateman et al. | |
| 6,107,626 A | 8/2000 | Wang et al. | |
| 6,124,137 A | 9/2000 | Hutchens et al. | |
| 6,204,500 B1 | 3/2001 | Whitehouse et al. | |
| 6,268,144 B1 | 7/2001 | Koster | |
| 7,332,296 B2 | 2/2008 | Elased et al. | |
| 7,834,313 B2 * | 11/2010 | Bystrom et al. | 250/282 |
| 8,039,794 B2 * | 10/2011 | Haddon et al. | 250/282 |
| 2006/0257861 A1 | 11/2006 | Elased et al. | |
| 2008/0166697 A1 | 7/2008 | Caulfield et al. | |
| 2009/0314936 A1 | 12/2009 | Okuno | |

FOREIGN PATENT DOCUMENTS

WO WO-2005/083113 9/2005

OTHER PUBLICATIONS

Baker et al:"Simultaneous Fragmentation of Multiple Ions Using IMS Drift Time Dependent Collision Energies", Journal of the American Society for Mass Spectrometry, Elsevier Science Ins, US, vol. 19, No. 3, Dec. 4, 2007 pp. 411-419, XP022517906.

Barber M et al: "Fast atom bombardment mass spectrometry of the angiotensin peptides", Biological Mass Spectrometry, vol. 9, No. 5, May 1, 1982 pp. 208-214, XP55005346.

Bruton J et al: "Sensitive and rapid determination of Angiotensin I utilizing on-line extraction and LC-MS/MS", Clinical Chemistry vol. 53, No. 6, Suppl. S, Jun. 2007 pp. A180-A181, XP008141545.

Bean et al, Tandem Mass Spectrometry of Peptides Using Hybrid and Four-Sector Instruments: A Comparative Study, Anal. Chem. 63:1473-1481, 1991.

(Continued)

*Primary Examiner* — Kiet T Nguyen
(74) *Attorney, Agent, or Firm* — Foley & Lardner LLP

(57) ABSTRACT

Provided are methods for measuring renin activity in a plasma sample using mass spectrometry. The methods generally involve ionizing purified angiotensin 1 from the sample and detecting the amount of angiotensin 1 ions generated. The amount of detected angiotensin 1 ions are then related to the amount of angiotensin 1 generated in the sample, which in turn is related to renin activity in the sample.

28 Claims, 14 Drawing Sheets

OTHER PUBLICATIONS

Cavalier et al, Cavalier et al, Analytical Veriation in Plasma Renin Activity: Implications for the Screening of Primary Aldosteronism, Clinical Chemistry, 53(4):803-804, 2007.

Christie, Solid-phase extraction columns in lipid analysis. Lipid Technology, 3:31-33 (1991) and 16-19 (2003) located at http://www.lipidlibrary.co.uk/topics/solid_pe/index/htm.

Compton D et al: "Detecting trace components in liquid chromatography/mass spectrometry data sets with two-dimensional wavelets", Proceedings of SPIE, vol. 6763, Jan. 1, 2007 pp. 67630p-67630p-12, XP55005348.

Derkx et al, More on Renin, Clin. Chem, 43(4):694-697, 1997.

Donoghue et al, A Novel Angiotensin-Converting Enzyme-Related Carboxypeptidase (ACE2) Converts Angiotensin I to Angiotensis 1-9, Circ. Res., 87:e1-e9, 2000.

Ferranti et al, Study of interaction of styrene oxide with Angiotensin by mass spectrometry, Carcinogenesis, vol. 13, No. 8, pp. 1397-1401, 1992.

Fredline et al. Measurement of Plasma Renin Activity with use of HPLC-electrospray-Tandem Mass Spectrometry, Clin. Chem. 45:659-664 (1999).

Funder et al, Case Detection, Diagnosis, and Treatment of Patients with Primary Aldosteronism: An Endocrine Sociiety Clinical Practice Guideline, J Clin Endocrinol Metab, 93(9):3266-3281, 2008.

Fyhrquist et al, Radioimmunoassay of Plasma Renin Activity, Clin. Chem., 22(2):250-256, 1976.

Grotemeyer J et al: "Peptides investigated by laser desorption-multiphoton ionization mass spectrometry", Organic Mass Spectrometry, vol. 23, No. 5, May 1, 1988 pp. 388-396, XP55005345.

Healy et al, Kidney Aminopeptidase A and Hypertension, Part I: Spontaneously Hypertensive Rats, Hypertension, 33:740-745, 1999.

Hermann et al, Measurement and Characterization of Angiotensin Peptides in Plasma, Clin. Chem., 34(6):1046-1051, 1988.

International Search Report dated Sep. 21, 2009 in related application PCT/US2009/53189.

Klickstein, L.B. and Wintroub, B.U., Separation of Angiotensins and Assay of Angiotensin-Generating Enzymes by High-Performance Liquid Chromatography, Anal Biochem 120: 146-150 (1982).

Kodish et al, Plasma renin concentration: comparision of angiotensianse inhibitors and correlation with plasma renin activity and aldosterone, JLCMAK 83(5):705-715, 1974.

Kohara et al., Reassessment of Plasma Angiotensins Measurement: Effects of Protease Inhibitors and Sample Handling Procedures, Peptides 12:1135-1141 (1991).

Kurtz et al, Identification of Plasma Angiotensinase as Aminopeptidase, Nature, 221:92-93, 1969.

Mallela J et al: "The functional importance of the N-terminal region of human prolylcarboxypeptidase", Biochemical and Biophysical Research Communications, Academic Press Inc. Orlando, FL, US, vol. 374, No. 4, Jul. 24, 2008 pp. 635-640, XP023976429.

Meng et al., Effects of Dietary Salt on Angiotensin Peptides in Kidney, J. Am. Soc. Nephrol. 6:1209-1215 (1995).

Meng et al., Simplified method for quantitation of angiotensin peptides in tissue, J. Chromatogr. 21, 614(1):19-25 (1993).

Merchant, M. and Weinberger, S.R., Recent advancements in surface-enhanced laser desorption/ionization-time of flight-mass spectrometry, Electrophoresis 21:1164-77 (2000).

Miyazaki et al., Determination of Renin Activity in Human Plasma by Column-Switching High-Performance Liquid Chromatography with Fluorescence Detection, J Chromatogr. 490: 43-51 (1989).

Mulder et al., Automated on-line solid-phase extraction coupled with HPLC for measurement of 5-Hydroxyindole-3-acetic acid in urine. Clinical Chemistry, 51:9, 1698-1703 (2005).

Nussberger et al, Specific Measurement of Angiotensin Metabolites and In Vitro Generated Angiotensin II in Plasma, Hypertension, 8:476-482, 1986.

Robb et al., Atmospheric Pressure Photoionization: An Ionization Method for Liquid Chromatography-Mass Spectrometry. Anal. Chem. 72(15):3653-3659 (2000).

Ryan et al, pH-Independent Inhibition of Plasma Angiotensis I Degradation: Implications for Renin Assay, Clinica Chimica Acta, 98:67-76, 1979.

Schwartz et al, Screening for Primary Aldosteronism in Essential Hypertension: Diagnostic Accuracy of the Ratio of Plasma Aldosterone Concentration to Plasma Renin Activity, Clin. Chem., 51(2):386-394, 2005.

Sealey et al, Plasma renin and aldosterone measurements in low renin hypertensive states, Trends in Endorinology and Metabolism, 16(3):86-91, 2005.

Sealey et al, Radioimmunoassay of Plasma Renin Activity, Seminars in Nuclear Medicine, 5(2):189-202, 1975.

Sealey, J.E., Plasma Renin Activity and Plasma Prorenin Assays, Clin. Chem., 37:1811-1819 (1991).

Shionoiri et al., Measurement of plasma active rennin by solid phase radioimmunoassay using monoclonal antibodies. Am J Med Sci, 300(3): 138-143, 1990.

Shionoiri et al., Renin gene expression in the adrenal and kidney of patients with primary aldosteronism. Journal of Clinical Endocrinology and Metabolism, 74: 103-107, 1992.

Sommer et al., Direct Measurement of Immunoreactive Renin during Changes of Posture in Man, Horm Res. 37:171-175 (1992).

Song et al, Kidney Aminopeptidase A and Hypertension, Part II: Effects of Angiotensin II, Hypertension, 33:746-752, 1999.

Tang et al, Fragmentation Reactions of Multiply-Protonated Peptides and Implications for Sequencing by Tandem Mass Spectrometry with Low-Energy Collision- Induced Dissociation, Anal. Chem. 65:2824-2834, 1993.

Tonna et al, Functional genetic variation in aminopeptidase A (ENPEP): lack of clear association with focal and segmental glomerulosclerosis FSGS, Gene, Author Manuscript; available in PMC Jul. 6, 2009, 20 pgs.

Ulmer and Meikle, Sample requirements for plasma rennin activity and immunoreactive rennin. Clinical Chemistry, 46(9): 1442-1444 (2000).

Voelker et al, Improved HPLC-Radioimmunoassay for Quantifying Angiotensin II In Plasma, Clin. Chem. 40(8):1537-1543, 1994.

Walsh et al, Proteases in blood clotting, Essays in Biochemistry—Proteases in Biology and Medicine, 38:95-111, 2002.

Wright et al., Proteinchip® surface enhanced laser desorption/ionization (SELDI) mass spectrometry: a novel protein biochip technology for detection of prostate cancer biomarkers in complex protein mixtures, Prostate Cancer and Prostatic Diseases 2:264-76 (1999).

Ye et al., Automated on-line custom-switching HPLC-MS/MS method with pea determination of nine environment phenols in urine. Anal. Chem. 77(16): 5407-5413, 2005.

Yi et al, Inhibition of Intrinsic Proteolytic Activities Moderates Preanalytical Variability and Instability of Human Plasma, Journal of Proteome Research, 6:1768-1781, 2007.

Yi et al, Intrinsic Peptidase Activity Causes a Sequential Multi-Step Reaction SMSR) in Digestion of Human Plasma Peptides, Journal of Proteome Research, 6:5112-5117, 2008.

Supplemental European Search Report for Appl. No. 09 80 5622.9 dated Sep. 5, 2011.

Notice of Allowance dated Sep. 20, 2011 for U.S. Appl. No. 12/715,343, filed Mar. 1, 2010.

Notice of Allowance dated Sep. 21, 2010 for U.S. Appl. No. 12/189,092, filed Aug. 8, 2008.

Non-Final Office Action dated Apr. 22, 2010 for U.S. Appl. No. 12/189,092, filed Aug. 8, 2008.

* cited by examiner

MASS SPECTROMETRY ASSAY FOR PLASMA-RENIN

CROSS-REFERENCE TO RELATED PATENT APPLICATIONS

This application is a continuation of U.S. application Ser. No. 12/715,343, filed Mar. 1, 2010, issued as U.S. Pat. No. 8,106,351, which claims priority from PCT Application No. PCT/US2009/053189 filed Aug. 7, 2009, which claims priority from U.S. application Ser. No. 12/189,092 filed Aug. 8, 2008 (U.S. Pat. No. 7,834,313), each of which is hereby incorporated by reference in its entirety, including all figures and tables.

FIELD OF THE INVENTION

The invention relates to the measurement of renin activity. In a particular aspect, the invention relates to methods for measurement of plasma renin activity by HPLC-mass spectrometry.

BACKGROUND OF THE INVENTION

The following description of the background of the invention is provided simply as an aid in understanding the invention and is not admitted to describe or constitute prior art to the invention.

As discussed in Fredline et al. *Clin. Chem.* 45: 659-664 (1999), renin is a proteolytic enzyme secreted into blood by the juxtaglomerular cells of the kidney. Renin acts on angiotensinogen, to produce a decapeptide referred to as angiotensin 1 (Ang1). Ang1 is further cleaved by angiotensin-converting enzyme to form an octapeptide, referred to as angiotensin 2 (Ang2). Ang2 stimulates cell growth, renal tubule transport of sodium, and aldosterone release. Ang2 is one of the most potent vasopressors in humans and plays an important role in blood pressure regulation. Direct measurement of Ang2 is difficult because of its very low circulating concentrations and extremely short half-life; Ang1, which is more stable than Ang2, provides a better analyte to measure the state of the renin-angiotensin system. Determination of a "plasma renin activity" (PRA) from the rate of generation of Ang1 is used clinically for the diagnosis and management of hypertension.

The classical method for the determining PRA is radioimmunoassay (RIA), see Sealey, *Clin. Chem.* 37:1811-1819 (1991); Shionoiri et al., *Horm Res.* 37:171-175 (1992). A typical radioimmunoassay is performed by the simultaneous preparation of a series of standard and unknown mixtures in test tubes, each containing identical concentrations of labeled antigen and specific antibody. After an appropriate reaction time, the antibody-bound (B) and free (F) fractions of the labeled antigen are separated by one of a variety of techniques. The B/F ratios in the standards are plotted as a function of the concentration of unlabeled antigen (standard curve), and the unknown concentration of antigen is determined by comparing the observed B/F ratio with the standard curve. Radioimmunoassay methods are based on competitive binding principles, and the antibodies used can undergo non-specific binding with other plasma proteins such as endogenous angiotensins. This potential cross-reactivity can cause overestimation of the PRA. Another approach is to use HPLC to isolate Ang1 from other angiotensins before quantification with RIA (see examples from Meng et al., *J. Am. Soc. Nephrol.* 6: 1209-1215 (1995); Meng et al., *J. Chromatogr.* 21, 614(1): 19-25 (1993); Kohara et al., *Peptides* 12: 1135-1141 (1991)). These HPLC methods for the quantification of Ang1 have been developed using ultraviolet, fluorescence and mass spectrometer detection (see examples from Klickstein et al. *Anal Biochem* 120: 146-150 (1982); Miyazaki et al. *J Chromatogr.* 490: 43-51 (1989) and Fredline et al. *Clin. Chem.* 45: 659-664 (1999)).

For example, Fredline et al. describes measurement of plasma renin activity with the use of HPLC-electrospray-tandem mass spectrometry. In doing this measurement, Fredline et al. incubates plasma samples in the presence of a water-sensitive enzyme inhibitor (i.e., phenylmethylsulphonyl fluoride (PMSF)) and measures the amount of angiotensin 1 generated during incubation by observing the collision induced dissociation of precursor ions with a (m/z) of 649.

SUMMARY OF THE INVENTION

The present invention provides methods for measuring the amount of angiotensin 1 and for measuring plasma renin activity in a sample by mass spectrometry, including tandem mass spectrometry.

In one aspect, methods are provided for measuring the amount of angiotensin 1 in a sample. The methods may include: (a) ionizing angiotensin 1 in the sample to produce one or more ions detectable by mass spectrometry; (b) detecting the amount of angiotensin 1 ion(s) by mass spectrometry, wherein the ions are selected from the group consisting of ions with a mass/charge ratio of $433.0\pm0.5$, $619.4\pm0.5$, $647.4\pm0.5$ and $1297\pm0.5$; and (c) using the amount of angiotensin 1 ion(s) detected to measure the amount of angiotensin 1 in the sample. In some embodiments, the limit of quantitation of the methods is less than or equal to 0.1 ng/mL; such as less than or equal to 0.05 ng/mL; such as about 0.03 ng/mL. In further embodiments, the method comprises purifying angiotensin 1 from the sample by high performance liquid chromatography (HPLC). In some embodiments, the methods further comprise purifying angiotensin 1 in the sample with a solid-phase extraction column. In other embodiments, the amount of the angiotensin 1 ion(s) is related to amount of angiotensin 1 in the sample by comparison to an internal standard. In some embodiments, a degradation standard may be used to determine the degree of degradation of angiotensin 1 during a renin activity assay.

In another aspect, methods are provided for measuring the amount of angiotensin 1 generated by renin in a sample. The methods may include: (a) ionizing angiotensin 1 from the sample to produce one or more ions; and (b) detecting the amount of at least one said ion(s) by mass spectrometry wherein said ion is selected from the group consisting of ions with a mass/charge ratio of $433.0\pm0.5$, $619.4\pm0.5$, $647.4\pm0.5$ and $1297\pm0.5$; and wherein the amount of angiotensin 1 ion(s) detected provides a measure of the amount of angiotensin 1 in the sample. In some embodiments, a degradation standard may be used to determine the degree of degradation of angiotensin 1 during a renin activity assay.

In another aspect, methods are provided for measuring the amount of angiotensin 1 in a sample. The methods may include: (a) incubating the sample premixed with a water stable protease inhibitor that is not effective against renin under conditions suitable for the generation of angiotensin 1 by renin in the sample; (b) purifying angiotensin 1 from the sample by liquid chromatography; (c) ionizing purified angiotensin 1 to produce one or more ions detectable by mass spectrometry; (d) detecting the amount of one or more angiotensin ion(s) by mass spectrometry, and (e) using the amount of ion(s) detected to measure the amount of angiotensin 1 in the sample. In some embodiments, the limit of quantitation of the method is less than or equal to 0.1 ng/mL; less than or equal to 0.05 ng/mL; and about 0.03 ng/mL. In further embodiments, the ions generated by mass spectrometry are selected from the group consisting of ions with a mass/charge ratio of 433.0±0.5, 619.4±0.5, 647.4±0.5 and 1297±0.5. In related embodiments, the ions comprise a precursor ion with a mass/charge ratio of 433.0±0.5, and one or more fragment ions selected from the group consisting of ions with a mass/charge ratio of 619.4±0.5 and 647.4±0.5. In other embodiments, the amount of angiotensin 1 ion(s) is related to the amount of angiotensin 1 in the test sample by comparison to an internal standard. In other embodiments, the methods further comprise purifying angiotensin 1 in the sample with a solid-phase extraction column. In other embodiments, the water stable protease inhibitor is aminoethylbenzylsulfonyl fluoride. In some embodiments, a degradation standard may be used to determine the degree of degradation of angiotensin 1 during a renin activity assay.

In another aspect, methods are provided for measuring the amount of angiotensin 1 in a sample. The methods may include: (a) incubating the sample under conditions suitable for the generation of angiotensin 1 by renin in the sample; (b) purifying angiotensin 1 from said sample by solid phase extraction; (c) further purifying angiotensin 1 following step (b) by liquid chromatography with on-line processing; (d) ionizing purified angiotensin 1 from step (c) to produce one or more ions detectable by mass spectrometry; and (e) detecting the amount of one or more angiotensin 1 ion(s) by mass spectrometry, (f) using the amount of ion(s) detected to measure the amount of angiotensin 1 in the sample. In some embodiments, the liquid chromatography is high performance liquid chromatography (HPLC). In other embodiments, the limit of quantitation of the methods is less than or equal to 0.1 ng/mL; less than or equal to 0.05 ng/mL; or about 0.03 ng/mL. In further embodiments, the methods include generating ions comprising one or more ions selected from the group consisting of ions with a mass/charge ratio of 433.0±0.5, 619.4±0.5, 647.4±0.5 and 1297±0.5. In related embodiments, the methods include generating precursor ions of angiotensin 1 in which at least one of the precursor ions has a mass/charge ratio of 433.0±0.5. In related embodiments, the methods may include generating one or more fragment ions of an angiotensin 1 precursor ion in which at least one of the fragment ions has a mass/charge ratio of 619.4±0.5 or 647.4±0.5. In further embodiments, the incubation occurs in the presence of a water stable protease inhibitor that is not effective against renin. In certain preferred embodiments, the water stable protease inhibitor is aminoethylbenzylsulfonyl fluoride. In some embodiments, the amount of angiotensin 1 ion(s) is related to the amount of angiotensin 1 in the test sample by comparison to an internal standard. In some embodiments, a degradation standard may be used to determine the degree of degradation of angiotensin 1 during a renin activity assay.

In another aspect, methods are provided for measuring renin activity in a sample. The methods may include: (a) incubating the sample under conditions suitable for the generation of angiotensin 1 by renin in the sample; (b) purifying angiotensin 1 from the sample by solid phase extraction; (c) further purifying angiotensin 1 by liquid chromatography with on-line processing; (d) ionizing purified angiotensin 1 to produce one or more ions detectable by mass spectrometry; (e) detecting the amount of one or more angiotensin 1 ion(s) by mass spectrometry; (f) using the amount of ion(s) detected to the amount of angiotensin 1 in the sample; and (g) using the quantity of angiotensin 1 in the sample to calculate renin activity in the sample. In some embodiments, the liquid chromatography is high performance liquid chromatography (HPLC). In another embodiments, the limit of quantitation of the methods is less than or equal to 0.1 ng/mL; less than or equal to 0.05 ng/mL; or about 0.03 ng/mL. In further embodiments, the methods include generating precursor ions of angiotensin 1 in which at least one of the precursor ions has a mass/charge ratio of 433.0±0.5, and generating one or more fragment ions of an angiotensin 1 precursor ion selected from the group consisting of ions with a mass/charge ratio of 619.4±0.5 or 647.4±0.5. In some embodiments, the incubation occurs in the presence of a water stable protease inhibitor. In related embodiments, the water stable protease inhibitor is aminoethylbenzylsulfonyl fluoride. In some embodiments, the amount of the angiotensin 1 ion(s) is related to the amount of angiotensin 1 in the test sample by comparison to an internal standard. In some embodiments, a degradation standard may be used to determine the degree of degradation of angiotensin 1 during a renin activity assay.

In another aspect, methods are provided for measuring renin activity in a sample. The methods include: (a) incubating the sample premixed with a water stable protease inhibitor that is not effective against renin under conditions suitable for the generation of angiotensin 1 by renin in the sample; (b) purifying angiotensin 1 by liquid chromatography; (c) ionizing the purified angiotensin 1 to produce one or more ions detectable by mass spectrometry; (d) detecting the amount of one or more angiotensin 1 ion(s) by mass spectrometry; (e) using the amount of ion(s) detected to measure the amount of angiotensin 1 in said sample; and (f) using the amount of angiotensin 1 in the sample to calculate renin activity in the sample. In some preferred embodiments, the liquid chromatography is high performance liquid chromatography (HPLC). In another embodiments, the limit of quantitation of the methods is less than or equal to 0.1 ng/mL; less than or equal to 0.05 ng/mL; or about 0.03 ng/mL. In further embodiments, the methods include generating precursor ions of angiotensin 1 in which at least one of the precursor ions has a mass/charge ratio of 433.0±0.5 and generating one or more fragment ions of an angiotensin 1 precursor ion from the group consisting of ions with a mass/charge ratio of 619.4±0.5 or 647.4±0.5. In some embodiments, step (b) comprises purification of angiotensin 1 from the sample with a solid-phase extraction column. In further embodiments, the water stable protease inhibitor is aminoethylbenzylsulfonyl fluoride. In some embodiments, a degradation standard may be used to determine the degree of degradation of angiotensin 1 during a renin activity assay.

In another aspect, methods are provided for measuring the renin activity in a sample. The methods include: (a) incubating the sample under conditions suitable for the generation of angiotensin 1 by renin in the sample; (b) purifying angiotensin 1 in the sample by liquid chromatography; (c) ionizing the purified angiotensin 1 to produce one or more ions detectable by mass spectrometry; (d) detecting the amount of the angiotensin 1 ion(s) by mass spectrometry, wherein the ion(s) are selected from the group consisting of ions with a mass/charge ratio of 433.0±0.5, 619.4±0.5, 647.4±0.5 and 1297±0.5; (e) using the amount of ion(s) detected to measure the amount of angiotensin 1 in said sample; and (f) using the amount of angiotensin 1 in the sample to calculate renin activity in the sample. In some embodiments, the limit of quantitation of the methods is less than or equal to 0.1 ng/mL; less than or equal to 0.05 ng/mL; or about 0.03 ng/mL. In some embodiments, the incubation occurs in the presence of a water stable protease inhibitor. In related embodiments, the water stable protease inhibitor is aminoethylbenzylsulfonyl fluoride. In some embodiments, the liquid chromatography is high performance liquid chromatography (HPLC). In some embodiments, step (b) of the method further comprises purification of angiotensin 1 with a solid-phase extraction column. In further embodiments, the amount of the angiotensin 1 ion(s) is related to the amount of angiotensin 1 in the test sample by comparison to an internal standard. In some embodiments, a degradation standard may be used to determine the degree of degradation of angiotensin 1 during a renin activity assay.

In some embodiments, if the PRA is less than 0.65 ng angiotensin per mL per hr after about 3 hours of incubation, the test sample may be incubated for a longer period of time (e.g. up to about 18 hours) to establish the PRA generation protocol.

Preferred embodiments utilize high performance liquid chromatography (HPLC), alone or in combination with one or more purification methods, for example but not limited to a solid phase extraction technique or protein precipitation, to purify angiotensin 1 in samples.

In certain embodiments of the methods disclosed herein, mass spectrometry is performed in positive ion mode. Alternatively, mass spectrometry can be performed in negative ion mode. In particularly preferred embodiments, angiotensin 1 is measured using both positive and negative ion mode. In certain preferred embodiments, angiotensin 1 is measured using electrospray ionization (ESI) or matrix assisted laser desorption ionization (MALDI) in either positive or negative mode.

In certain embodiments, the angiotensin 1 ions detectable in a mass spectrometer are selected from the group consisting of ions with a mass/charge ratio (m/z) of 1297±0.5, 756±0.5, 649±0.5, 647.4±0.5, 619.4±0.5, 534±0.5, 506±0.5, 433.0±0.5, 343±0.5, 255±0.5, and 110±0.5. In particularly preferred embodiments, the precursor ions have a mass/charge ratio of 433.0±0.5, and the fragment ions have a mass/charge ratio of 619.4±0.5 or 647.4±0.5.

In certain embodiments, a separately detectable isotope-labeled angiotensin 1, is added to the sample as an internal standard. In these embodiments, all or a portion of both the endogenous angiotensin 1 and the internal standard present in the sample is ionized to produce a plurality of ions detectable in a mass spectrometer, and one or more ions produced from each are detected by mass spectrometry. In related embodiments, the isotope labeled angiotensin 1 may comprise $^{13}C$ and $^{15}N$ isotope labeled valine, arginine, isoleucine, leucine, lysine, phenylalanine proline subunits or combinations thereof In further preferred embodiments, the isotope labeled angiotensin 1 has the valine subunit where carbon atoms are substituted with $^{13}C$ isotopes and the nitrogen atom is replaced with $^{15}N$ isotopes leading to an increase in mass of 6 Da relative to natural angiotensin 1. In related preferred embodiments, the isotope labeled angiotensin 1 has valine and isoleucine subunits where carbon atoms are substituted with $^{13}C$ isotopes and the nitrogen atoms are replaced with $^{15}N$ isotopes. The mass of this isotope labeled angiotensin 1 is nominally 13 Da higher than natural angiotensin 1.

In preferred embodiments, the presence and/or amount of the angiotensin 1 ion(s) is related to the presence and/or amount of angiotensin 1 in the test sample by comparison to the internal standard.

In certain preferred embodiments of the aspects disclosed herein, the limit of quantitation (LOQ) of angiotensin 1 is less than or equal to 0.1 ng/mL; such as less than or equal to 0.05 ng/mL; such as about 0.03 ng/mL; and the upper limit of quantitation (ULOQ) of angiotensin 1 is greater than or equal to 100,000 fmol/mL.

In another aspect, kits are provided for an angiotensin 1 quantitation assay. The kits comprise aminoethylbenzylsulfonyl fluoride (AEBSF) in phosphate buffered saline solution, wherein said AEBSF in phosphate buffered saline solution is present in amounts sufficient for at least one assay. The kits may additionally comprise internal standard and maleic acid in amounts sufficient for at least one assay.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Samples may be purified herein by various means to allow removal of one or more interfering substances, e.g., one or more substances that would interfere with the detection of selected angiotensin 1 parent and daughter ions by mass spectrometry.

As used herein, the term "test sample" refers to any sample that may contain angiotensins. As used herein, the term "body fluid" means any fluid that can be isolated from the body of an individual. Examples of body fluids include blood, plasma, serum, bile, saliva, urine, tears, perspiration, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of separation techniques which employ "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography). In some embodiments, an SPE column may be used in combination with an LC column. For example, a sample may be purified with a TFLC extraction column, followed by additional purification with a HPLC analytical column.

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including utilization of a turbulent flow liquid chromatography (TFLC) column as an extraction column, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. In a preferred embodiment the analytical column contains particles of about 4 μm in diameter.

As used herein, the term "on-line" or "inline," for example as used in "on-line automated fashion" or "on-line extraction," refers to a procedure performed without the need for operator intervention. For example, by careful selection of valves and connector plumbing, the solid phase extraction and liquid chromatography columns can be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of multi-well or multi-tube samples in an autosampler and the remaining operations are performed under computer control, resulting in purification and analysis of all samples selected. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z." MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces"; U.S. Pat. No. 6,107,623, entitled "Methods and Apparatus for Tandem Mass Spectrometry"; U.S. Pat. No. 6,268,144, entitled "DNA Diagnostics Based On Mass Spectrometry"; U.S. Pat. No. 6,124,137, entitled "Surface-Enhanced Photolabile Attachment And Release For Desorption And Detection Of Analytes"; Wright et al., *Prostate Cancer and Prostatic Diseases* 2:264-76 (1999); and Merchant and Weinberger, *Electrophoresis* 21:1164-67 (2000).

As used herein, the term "operating in positive ion mode" refers to those mass spectrometry methods where positive ions are generated and detected. The term "operating in negative ion mode" as used herein, refers to those mass spectrometry methods where negative ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., Atmospheric pressure photoionization: An ionization method for liquid chromatography-mass spectrometry. *Anal. Chem.* 72(15): 3653-59 (2000).

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification", "limit of quantitation" or "LOQ" refers to the point where measurements become quantitatively meaningful. The analyte response at this LOQ is identifiable, discrete and reproducible with a precision of 20% and an accuracy of 80% to 120%. The upper limit of quantitation refers to the upper quantifiable linear range of analyte response.

As used herein, the term "limit of detection" or "LOD" is the point at which the measured value is larger than the uncertainty associated with it. The LOD is defined arbitrarily as 3 standard deviations (SD) from the zero concentration.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.5 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
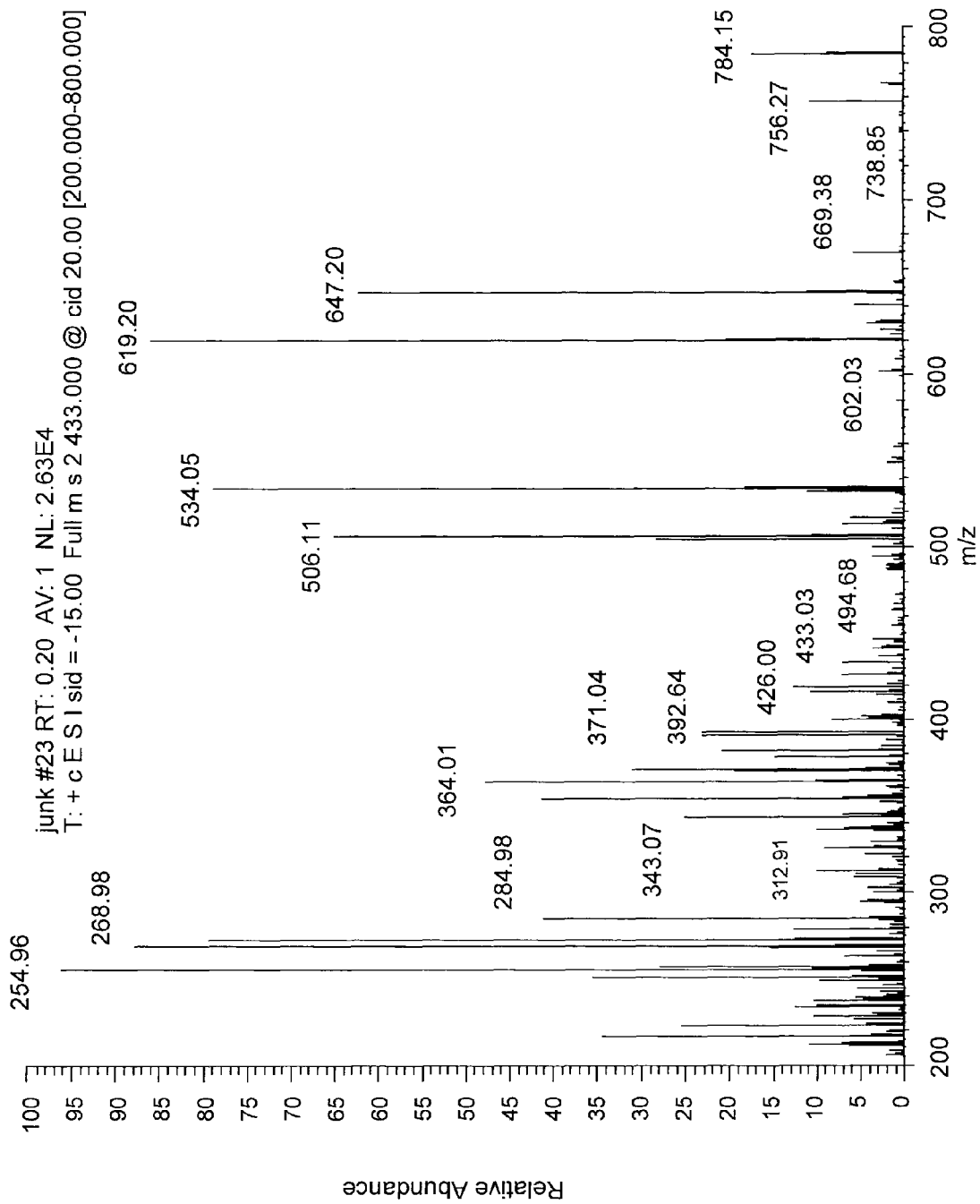
FIG. 1 shows collision-induced dissociation full scan spectra for Ang1 (m/z=433.0).
Figure 2:
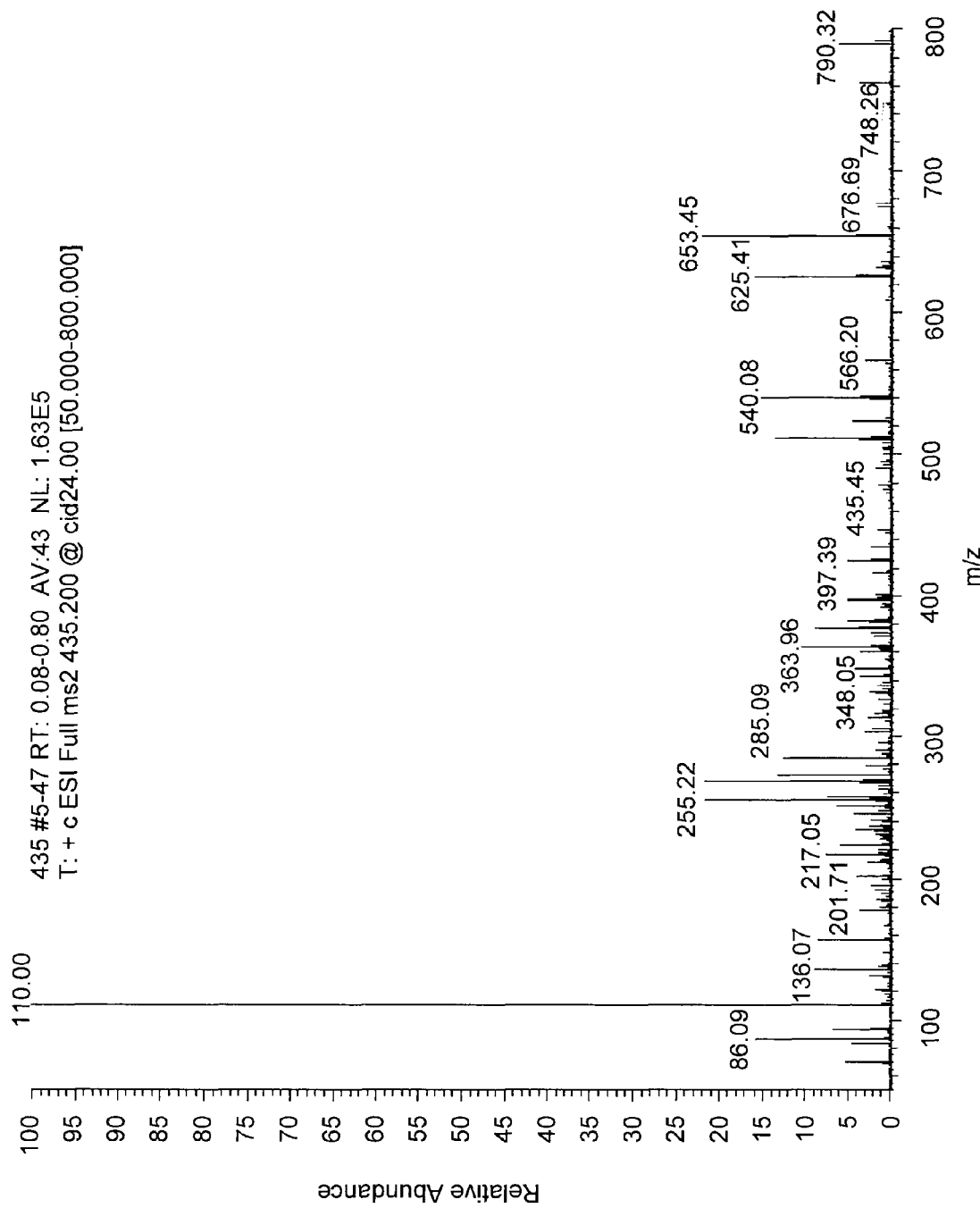
FIG. 2 shows collision-induced dissociation full scan spectra for internal standard (m/z=434.8).

Methods are described for measuring the amount of angiotensin 1 in a sample. More specifically, methods are described for detecting and quantifying angiotensin 1 related to renin activity in a plasma sample. The methods utilize liquid chromatography (LC), most preferably HPLC, to perform a purification of selected analytes, and combine this purification with unique methods of mass spectrometry (MS), thereby providing a high-throughput assay system for detecting and quantifying angiotensin 1 in a test sample. The preferred embodiments are particularly well suited for application in large clinical laboratories for automated PRA assay. The methods provided have enhanced sensitivity and are accomplished in less time and with less sample preparation than required in other PRA assays.

Suitable test samples include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include blood, plasma, serum, saliva, cerebrospinal fluid, or other tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum or plasma. To avoid irreversible cryoactivation of plasma prorenin, samples should be processed immediately at room temperature or stored completely frozen and quickly thawed just prior to use.

Various incubation conditions may be used to facilitate the preparation and generation of angiotensin 1 by renin prior to chromatography and or MS sample analysis so that the analysis can be automated. The current invention incorporates a single addition of a reagent cocktail suitable to perform the generation of angiotensin 1. The reagent cocktail is made from pre-mixing all the reagents in one simple step. This single generation of a reagent cocktail is achieved by replacing the typically utilized water-sensitive enzyme inhibitor, e.g., phenylmethylsulphonyl fluoride (PMSF), with a water stable, e.g., aminoethylbenzylsulfonyl fluoride (AEBSF). This is especially useful in automation for a large sample size because the labor intensive assay setup requires mixing of the water based reagents and a water-sensitive enzyme inhibitor, e.g., PMSF. This sequential addition requires vigorous stirring between each step to ensure homogeneity in the reagent solution before incubation. Furthermore, PMSF should be prepared fresh because PMSF is unstable in aqueous media. AEBSF has the added benefit of being much less toxic than PMSF. According to current invention, the reagent cocktail comprising the water-stable AEBSF has an unexpected long stability profile compared to a PMSF stock solution. The AEBSF-containing regent cocktail can be stored at −20° C. for up to approximately 6 months or at room temperature for approximately a week.

The present invention contemplates kits for an angiotensin 1 quantitation assay. A kit for an angiotensin 1 quantitation assay of the present invention may include a kit comprising AEBSF in phosphate buffered saline solution, in amounts sufficient for at least one assay. Kits contemplated by the present invention may also comprise isotope labeled internal standard and maleic acid. If inclusion of a degradation standard is desired in the kits, generation buffer can be included that comprises maleic acid, AEBSF and degradation standard. Typically, the kits will also include instructions recorded in a tangible form (e.g., contained on paper or an electronic medium) for using the packaged solutions for use in a measurement assay for determining the amount of angiotensin 1.

The calibration and QC pools were prepared using mock serum consisting of phosphate buffered saline supplemented with bovine serum albumin at 45 mg/mL. No source of human or non-human plasma or stripped serum was identified that did not contain measurable amounts of angiotensin 1.

Typically, the frozen plasma samples and controls are thawed rapidly to prevent cryoactivation of prorenin to renin before incubation. The sample is incubated at 37° C. for up to about 3 h. If the resulting sample does not yield a satisfactory PRA measurement, the incubation time can be extended to up to about 18 h. Samples are then frozen (for example, brought to a temperature of about −20° C.) to stop the incubation and stored in this state until analysis. According to current invention, plasma renin may be incubated at 37° C.±1° with endogenous renin substrate (angiotensinogen) at pH 5.7 for about 1 to 2 hours in the presence of converting enzyme, degradation standard (valine and isoleucine isotope labeled angiotensin 1) and angiotensinase inhibitors (EDTA and AEBSF).

After the conclusion of incubation, the samples may be subject to liquid-liquid extraction or solid phase extraction before LC purification. In the present invention, extraction of angiotensin 1 is adapted utilizing a suitable solid phase extraction column coupled (either on-line or offline) with HPLC. According to preferred embodiments, the method involves adding formic acid to each sample after incubation and loading samples directly onto the solid-phase extraction column coupled with HPLC-mass spectrometer.

Liquid chromatography (LC) including high-performance liquid chromatography (HPLC) relies on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with angiotensin 1. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-8 or C-18 bonded groups. The chromatographic column includes an inlet port for receiving a sample directly or indirectly from coupled SPE column and an outlet port for discharging an effluent that includes the fractionated sample. In one embodiment, the sample (or pre-purified sample) may be applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In another embodiment, the solid-phase extraction (SPE) column may be employed before HPLC on a hydrophobic column chromatographic system. In certain preferred embodiments, a column comprising polymeric sorbents may be coupled on-line with a HPLC system. In certain preferred embodiments, purification of the sample with a SPE column and HPLC are performed using HPLC Grade Ultra Pure 0.1% formic acid in water and 0.1% formic acid in acetonitrile as the mobile phases. Preferably, the SPE column used in these embodiments is capable of recovering more than 80% of angiotensin from plasma.

By careful selection of valves and connector plumbing, one or more solid phase extraction and chromatographic columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

Mass spectrometry is performed using a mass spectrometer, which includes an ion source for ionizing the fractionated sample and creating charged molecules for further analysis. In various embodiments, angiotensin 1 present in a test sample may be ionized by any method known to the skilled artisan. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, angiotensin 1 may be ionized by electrospray ionization (ESI) or matrix assisted laser desorption ionization (MALDI). In further preferred embodiments, angiotensin 1 is ionized by heated electrospray ionization (HESI) in positive mode.

After the sample has been ionized, the positively charged or negatively charged ions thereby created may be analyzed to determine a mass-to-charge ratio. Suitable analyzers for determining mass-to-charge ratios include triple quadrupole analyzers, quadrupole analyzers, ion traps analyzers, fourier transform analyzers, orbitrap analyzers and time-of-flight analyzers. The ions may be detected using several detection modes. For example, selected ions may be detected using a scanning mode, e.g., highly selectively reaction monitoring (H-SRM), multiple reaction monitoring (MRM) or selected reaction monitoring (SRM), or alternatively, ions may be detected using a selective ion monitoring mode (SIM). Preferably, the mass-to-charge ratio is determined using a triple quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument. A linear series of three quadrupoles are known as a triple quadrupole mass spectrometer. The first (Q1) and third (Q3) quadrupoles act as mass filters, and the middle (Q2) quadrupole is employed as a collision cell. This collision cell is an RF only quadrupole (non-mass filtering) using He, Ar, or N gas (~$10^{-3}$ Torr, ~30 eV) to induce collisional dissociation of selected parent ion(s) from Q1. Subsequent fragments are passed through to Q3 where they may be filtered or scanned fully.

One may enhance the selectivity of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of angiotensin 1. Methods of generating and using such standard curves are well known in the art and one of ordinary skill is capable of selecting an appropriate internal standard. For example, an isotope labeled angiotensin 1 may be used as an internal standard; in certain preferred embodiments the standard is isotope labeled angiotensin 1 where the valine subunit has been fully substituted with valine where the carbon atoms have been substituted with $^{13}C$ isotopes and the nitrogen atoms have been replaced with $^{15}N$ isotopes. Numerous other methods for relating the amount of an ion to the amount of the original molecule will be well known to those of ordinary skill in the art.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In certain embodiments, angiotensin 1 is quantitated using MS/MS as follows. Samples are subjected to liquid chromatography, preferably a solid phase extraction column followed by HPLC, the flow of liquid solvent from the chromatographic column enters the heated nebulizer interface of an MS/MS analyzer and the solvent/analyte mixture is converted to vapor in the heated tubing of the interface. The analyte (e.g., angiotensin 1), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of angiotensin 1. Precursor ions with the correct mass/charge ratios of angiotensin 1 are allowed to pass into the collision chamber (Q2), while unwanted ions with any other mass/charge ratio collide with the sides of the quadrupole and are eliminated. Precursor ions entering Q2 collide with neutral collision gas molecules, for example argon gas molecules, and fragment. This process is called collision activated dissociation (CAD). The fragment ions generated are passed into quadrupole 3 (Q3), where the fragment ions of angiotensin 1 are selected while other ions are eliminated.

The methods may involve MS/MS performed in either positive or negative ion mode. Using standard methods well known in the art, one of ordinary skill is capable of identifying one or more fragment ions of a particular precursor ion of angiotensin 1 that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (angiotensin 1) of interest. In certain embodiments, the area under the curves, or amplitude of the peaks, for fragment ion(s) and/or precursor ions are measured to determine the amount of angiotensin 1. As described above, the relative abundance of a given ion may be converted into an absolute amount of the original analyte, e.g., angiotensin 1, using calibration standard curves based on peaks of one or more ions of an internal molecular standard, such as isotope labeled angiotensin 1.

These data may be relayed to a computer, which generates plots of ion count versus time. The areas under the peaks are determined and calibration curves are constructed by plotting standard concentration versus peak area ratio of Ang1/internal standard. Using the calibration curves, the amount of angiotensin 1 and selected internal standards in the sample is determined. The rate of angiotensin 1 formation over a given time, i.e., the amount of angiotensin 1 formed during sample incubation, can be calculated from these determinations. This rate is an indication of renin activity in the sample.

The basic process of reducing data can be performed manually or with the assistance of computer software. The dilution of plasma and generation time are taken into account in determining the final PRA value according to the following calculation:

$$\frac{x\,uL\text{ plasma} + y\,uL\text{ buffer}}{x\,uL\text{ plasma}} * \frac{1}{z\text{ hours}} = f$$

wherein x is the volume of the plasma sample; y is the volume of buffer added and z is the time for sample incubation.

The result from LCquan reported as ng/mL is then multiplied by f to give a corrected measurement for the PRA assay in ng per mL per hr. If the sample has been diluted to bring the final result into the linear range of the assay, the final result is also multiplied by the degree of dilution.

Some plasma samples have a high degree of enzymatic activity which degrades angiotensin 1 during a renin activity assay. In some embodiments, a degradation standard may be used to determine the degree of degradation of angiotensin 1 that has occurred during generation of angiotensin 1 by renin. In these embodiments, the degradation standard is added to the sample prior to incubation. Procedurally, this differs from the timing of adding an internal standard, which is added after incubation but prior to mass spectrometric analysis. In some embodiments, the degree of degradation may be determined by comparison of the measured quantity of degradation standard (after incubation) with the measured quantity of internal standard. In other embodiments, the degree of degradation may be determined by identifying and quantifying species in the sample that are generated by the breakdown of the degradation standard. Typically, breakdown products useful for monitoring are essentially absent from the sample but for the breakdown of the degradation standard. The degradation standard may be a synthetic peptide which incorporates one or more $^{13}C$ and/or $^{15}N$ labeled amino acids, that when ionized produces at least one ion with a m/z different than ions produced by ionizing unlabeled angiotensin 1 and the internal standard. Calculation of a degradation factor in such embodiments requires further consideration. In embodiments where the measured amount of degradation standard remaining after incubation is compared to the measured amount of internal standard, the percent degradation may be calculated as follows.

First, the baseline ratio (BR) is calculated by calculating the ratio of the average area of degradation standard (DS) to analytical internal standard (IS) for the three Bio-Rad QC samples:

$$\frac{\text{Low } DS}{\text{Low } IS} + \frac{\text{Med } DS}{\text{Med } IS} + \frac{\text{High } DS}{\text{High } IS} \times \frac{1}{3} = \text{baseline ratio } (BR)$$

Then, the % degradation for each patient sample is calculated:

$$\frac{DS}{IS} \times \frac{1}{BR} \times 100 = \%\text{ degradation}$$

In embodiments where generation of breakdown products of the degradation standard are quantitated, MRM transitions to monitor with tandem mass spectrometry may be identified by scanning for precursor ions associated with N- or C-terminal directed degradation of the degradation standard. Degradation standards may be selected such that these precursor ions may be identified by their characteristic fragmentation into known fragment ions. For example, in some embodiments, the degradation standard may comprise isotope-labeled Ang1 peptides. Preferred isotope-labeled Ang1 peptides include those containing one or more modified amino acid residues selected from the group consisting of modified valine, isoleucine, proline, or histidine. In embodiments where the degradation standard comprises isotope-labeled Ang1 peptides containing modified proline or histidine, Q3 may be set to select for immonium ions of isotope-labeled proline or histidine, while Q1 is scanned over m/z ranges that would be associated with N- or C-terminal degradation of the labeled Ang1 peptides. Quantitation may be accomplished by use of total ion current resulting from such precursor ion scans.

The following examples serve to illustrate the invention. These examples are in no way intended to limit the scope of the methods.

EXAMPLES

Example 1

Sample and Reagent Preparation

Reagents: angiotensin 1, aminoethylbenzylsulfonyl fluoride (AEBSF), bovine serum albumin (protease free), maleic anhydride, phosphate buffered saline tablets (PBS tablets), formic acid, and Bio-Rad Lyphocheck controls were purchased from their respective suppliers. Isotope labeled Ang1 standards were custom synthesized. The internal standard was the single isotope labeled Ang1 where natural valine is wholly substituted with valine containing $^{13}C$ and $^{15}N$ atoms leading to a mass difference of +6 Da. Similarly, the degradation standard used in the assay was double isotope labeled Ang1 where natural valine and isoleucine are wholly substituted with valine and isoleucine containing $^{13}C$ and $^{15}N$ atoms leading to a mass difference of +13 Da.

The analytical internal standard (including degradation standard) may be a synthetic peptide which incorporates one or more $^{13}C$ and/or $^{15}N$ labeled amino acids. The primary sequence of the internal standard used in this example is valine-isotope labeled Ang1, DR[$V^{15}N$, $^{13}C$]YIHPFHL. Synthesis was accomplished at the 2-5 mg scale with a final purity specification of >95%. The peptide was packaged in individual aliquots with a total peptide content of 2 nmol per vial. In addition, a degradation standard with valine and isoleucine-isotope labeled Ang1, i.e. DR[$V^{15}N$, $^{13}C$]Y[$I^{15}N$, $^{13}C$]HPFHL, was prepared. Synthesis was accomplished at the 2-5 mg scale with a final purity specification of >95%. The peptide was packaged in individual aliquots with a total peptide content of 2 nmol per vial.

Doubly distilled deionized water and HPLC-grade methanol and acetonitrile were used throughout the investigation. Mock serum were prepared according to the following procedure. First, 300 mL of water was added to a graduated cylinder along with two PBS tablets. Then, 22.5 g of bovine serum albumin was added and thoroughly mixed. Next, 0.02 g AEBSF was added and thoroughly mixed. Finally, sufficient water was added to reach a final volume of 500 mL.

Preparation of generation cocktail, i.e., incubation solution, is dependent on the number of samples in a given assay setup. The volumes indicated in Table 1 (below) include a 20% excess to assure sufficient volume for transfer. Maleic acid, AEBSF, and degradation standard (e.g. DR[$V^{15}N$, $^{13}C$]Y[$I^{15}N$, $^{13}C$]HPFHL) were mixed in a 15 mL PP tube.

TABLE 1

Volumes useful for preparing generation cocktails.

| No. of samples | Maleic acid | AEBSF stock | Degradation standard |
|---|---|---|---|
| 150 | 4.75 mL | 250 uL | 22 uL |
| 225 | 7.13 mL | 375 uL | 33 uL |
| 300 | 9.5 mL | 500 uL | 44 uL |

AEBSF stock solution was evaluated for its stability. 0.91 grams of AEBSF powder was placed into a 15 mL Corning tube and dissolved with 10 mL of peptide solvent. 0.5 mL aliquots of this solution were placed into 1.5 mL Nunc cyrovials. Stored in this way, the solution was found to be stable for up to about 6 months when stored at −20° C., or for about one week when stored at room temperature.

Example 2

Calibrators and Controls

Calibrators was prepared by spiking known amounts of angiotensin 1 into matrix using mock serum. The concentration of the calibration series was 0.0 (blank), 0.14, 0.27, 1.1, 2.19, 8.79, 35.15, and 43.2 ng/mL. QC pools were prepared at 1.1, 8.7, and 35 ng/mL. Controls were obtained from BioRad and consisted of samples with high, intermediate, and low renin activity. QC pools and calibrators were ran with each sample batch for quality assurance.

Example 3

Preparation of Samples for Generation

The frozen samples were quickly brought to room temperature using a fan or room temperature water bath. The specimens were intermittently inverted to hasten the thawing process as quick thawing is critical to prevent the cryoactivation of prorenin to renin. The samples were allowed to remain at room temperature once thawed. All plasma samples were vortexed thoroughly prior to testing.

Example 4

Incubation Procedure 250 uL of EDTA plasma was mixed with 25 uL of generation cocktail (0.275 M Maleic acid, 1 mM AEBSF, 4 uM degradation standard). Samples were incubated at about 37 degrees for about 1-3 hours and subsequently mixed with an approximately equal volume of 10% formic acid containing 2 uM analytical internal standard.

Example 5

Purification of Angiotensin I from Test Sample

All chromatographic steps were carried out using a Cohesive TLX four channel system.

100 uL of acidified sample was injected onto a 2.1 mm×20 mm 25 uM HLB extraction cartridge using a solvent A (0.1% Formic acid in water). The extraction cartridge was eluted using 100 uL of and 80:20 mixture of solvent A (0.1% Formic acid in water) and solvent B (0.1% Formic acid in acetonitrile). The eluate was mixed at a ratio of 1:3 with solvent A and directed to a 2.1 mm×50 mm 5 uM Xbridge 130 BEH analytical column. After transfer of the analyte to the analytical column, a gradient from 95% A to 65% solvent A was developed. At the appropriate time during the gradient, the flow was diverted from waste and directed to the mass spectrometer. Both the extraction cartridge and analytical column were cleaned and re-equilibrated in-situ before the next injection.

Example 6

Detection and Quantitation of Angiotensin 1 by MS/MS

MS/MS was performed using a TSQ Quantum Ultra with a HESI (Heated Electrospray Ionization) source in positive ion mode. Selected reaction monitoring was used for quantitative analysis of the analyte and internal standards. Six transitions were monitored, two for each of analyte, analytical internal standard, and degradation standard. Peak area ratios between analyte and internal standard were calibrated against a series of known angiotensin 1 stocks and calibration curves were then constructed using a 1/x weighted linear regression. Selected MS/MS parameters are listed in Table 2, below:

TABLE 2

Selected MS/MS parameters.

| | |
|---|---|
| Ionization voltage | 3000 V |
| Vaporizer Temperature | 300° C. |
| Sheath Gas | 30 units |
| Ion Sweep Gas Pressure | 0 |
| Auxiliary Gas Pressure | 30 units |
| Capillary Temperature | 350° C. |
| Tube Lens Offset | 110 |
| Skimmer Offset | 0 to −5 V |
| Collision Pressure | 1.5 mTorr |
| Collision Energy | 16 V (433→619) |
| | 22 V (433→647) |

Ions passed to the first quadrupole (Q1), which was set to select ions with a mass to charge ratio of 433.0±0.5 m/z $[M+3H]^{3+}$. Ions entering quadrupole 2 (Q2) collided with argon gas to generate ion fragments, which were passed to quadrupole 3 (Q3) for further selection. Simultaneously, the same process using isotope dilution mass spectrometry was carried out with an isotope labeled angiotensin 1 internal standard or a isotope labeled angiotensin 1 degradation standard. The following mass transitions were used for detection and quantitation during validation on positive polarity.

TABLE 3

Mass Transitions for angiotensin 1 (Positive Polarity)

| Analyte | Precursor Ion (m/z) | Product Ions (m/z) |
|---|---|---|
| Angiotensin I | 433.0 ± 0.5 | 647.4 ± 0.5, |
| | $[M + 3H]^{3+}$ | 619.4 ± 0.5 |
| Internal Standard | 434.8 ± 0.5 | 653.4 ± 0.5, |
| (DR[V$^{15}$N, $^{13}$C]YIHPFHL) | $[M + 3H]^{3+}$ | 625.5 ± 0.5 |
| Degradation Standard | 437.3 ± 0.5 | 660.4 ± 0.5, |
| (DR[V$^{15}$N, $^{13}$C]Y[I$^{15}$N, $^{13}$C]HPFHL) | $[M + 3H]^{3+}$ | 631.4 ± 0.5 |

Figure 3:
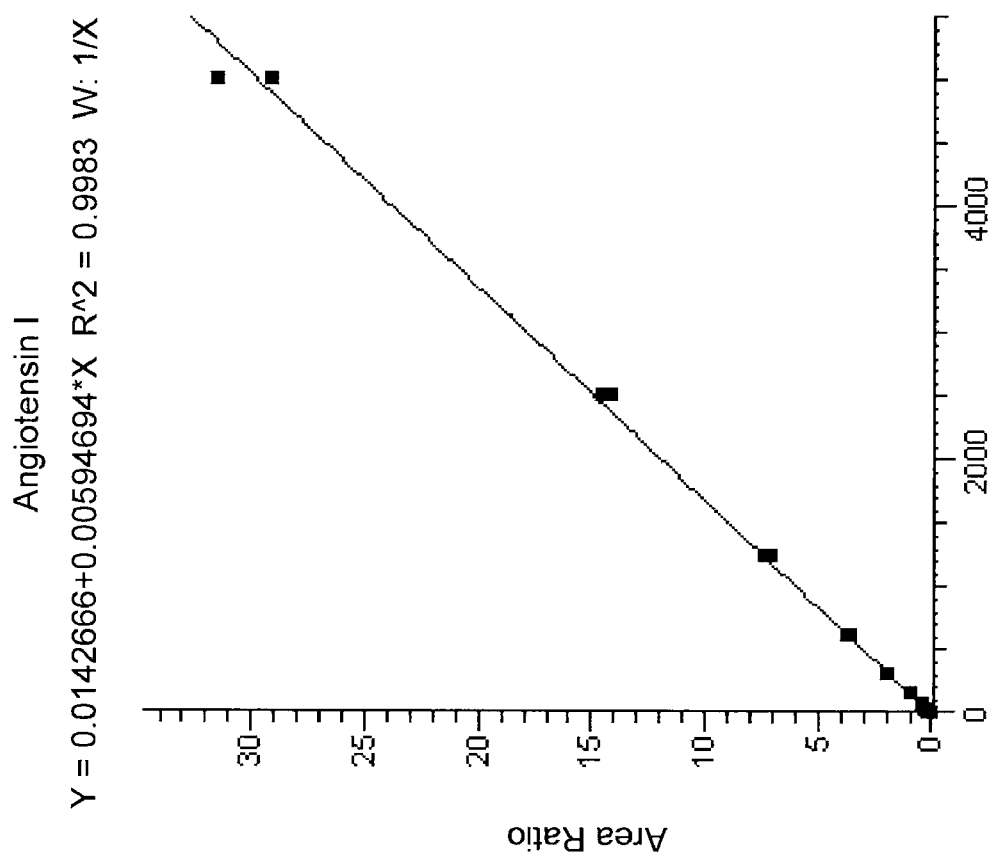
FIG. 3 shows an exemplary calibration curve for the mass spectrometric detection of Ang1.
Figure 4:
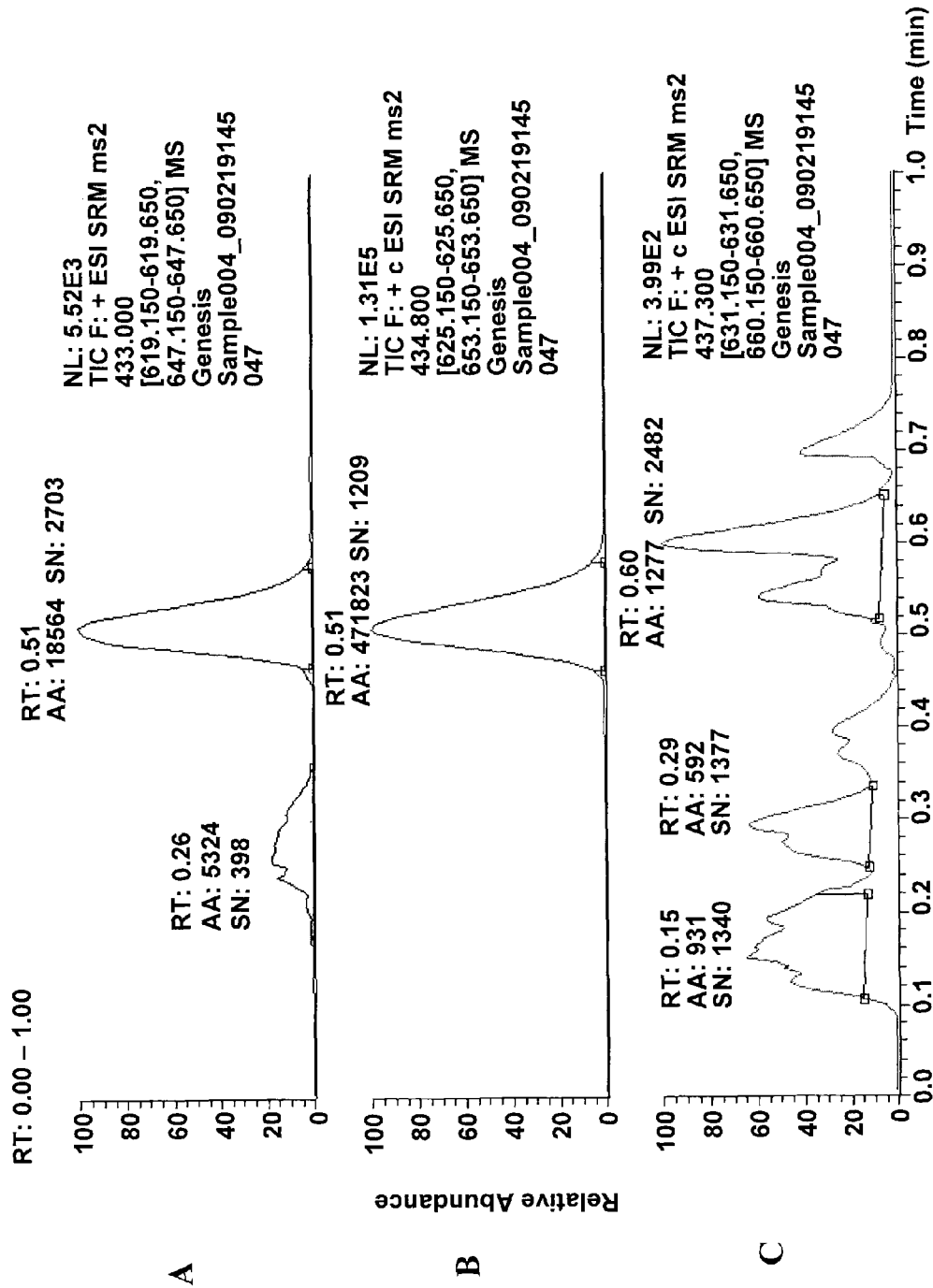
FIGS. 4A, B, and C show exemplary mass chromatograms of Ang1 (m/z=433.0±0.5), internal standard (m/z=434.8±0.5), and degradation standard (m/z=437.3±0.5), respectively, for a low concentration calibrator.
Figure 5:
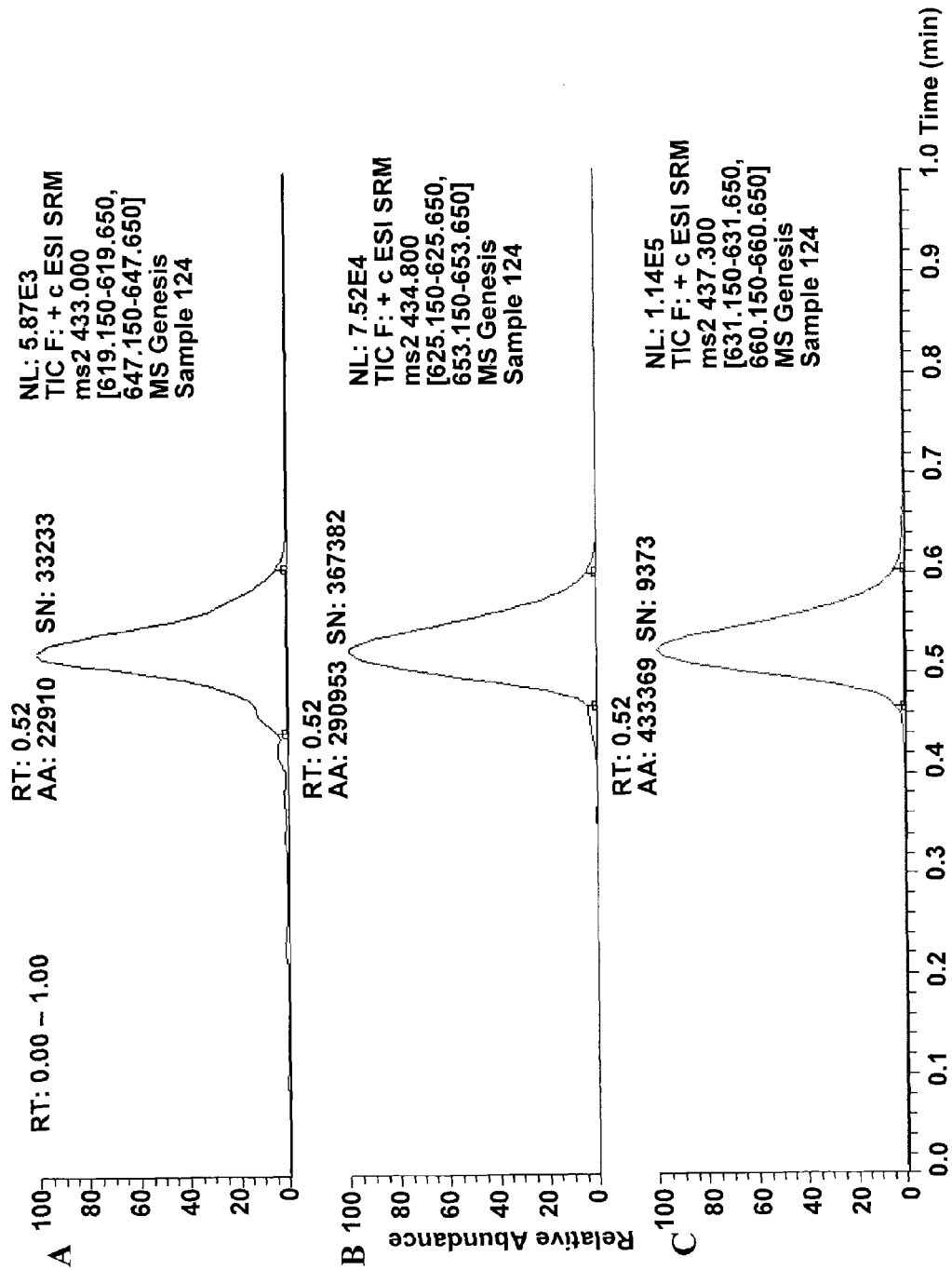
FIGS. 5A, B, and C show exemplary mass chromatograms of Ang1 (m/z=433.0±0.5), internal standard (m/z=434.8±0.5), and degradation standard (m/z=437.3±0.5), respectively, for a patient sample demonstrating 0.1 ng/mL/hr.

These data were relayed to a computer, which generated plots of ion count versus time. The areas under the peaks were determined and calibration curves were constructed by plotting standard concentration versus peak area ratio of analyte/internal standard. Using the calibration curves, the concentrations of angiotensin 1 and selected internal standards were quantitated for samples. An exemplary calibration curve is shown in FIG. 3. Exemplary mass chromatograms of Ang1 (m/z=433.0±0.5), internal standard (m/z=434.8±0.5), and degradation standard (m/z=437.3±0.5), respectively, for a low concentration calibrator are shown in FIGS. 4A, B, and C. Similarly, FIGS. 5A, B, and C show exemplary mass chromatograms of Ang1 (m/z=433.0±0.5), internal standard (m/z=434.8±0.5), and degradation standard (m/z=437.3±0.5), respectively, for a patient sample demonstrating 0.1 ng/mL/hr PRA.

Example 7

Intra-Assay and Inter-Assay Precision and Accuracy

Eight aliquots from each of the three QC pools were analyzed in a single assay to determine the reproducibility (CV) of a sample within an assay. The following values were determined:

TABLE 4

Inter- and Intra-Assay Variation

| | Low QC (1.1 ng/mL) | Med. QC (8.7 ng/mL) | High QC (35 ng/mL) |
|---|---|---|---|
| Inter-assay | 6.04% | 6.96% | 5.64% |
| Intra-assay | 6.18% | 5.14% | 5.09% |

Example 8

Analytical Sensitivity: Limit of Detection (LOD) and Limit of Quantitation (LOQ)

The limit of detection (LOD) is the point at which a measured value is larger than its associated uncertainty. The angiotensin 1 zero standard was run in 17 replicates and the resulting area ratios were back calculated to a concentration based on the calibrators to determine the limit of detection of the assay. The limit of detection (LOD) for the angiotensin 1 assay was 30 fmol/mL.

To determine the limit of quantitation (LOQ) with a precision of 20% and an accuracy of 80% to 120%, five different samples at concentrations close to the expected LOQ were assayed and the reproducibility determined for each. The LOQ for the angiotensin 1 assay was defined at 0.03 ng/mL Example 9

Assay Reportable Range and Linearity

To establish the linearity of angiotensin 1 detection in the assay, one blank assigned as zero standard and eight spiked artificial serum samples (calibrators) were prepared and analyzed on five separate days. A weighted (1/x) linear regression from five consecutive runs yielded coefficient correlation of 0.995 or greater, with an accuracy of ±20% revealing a quantifiable linear range of 77 to 100,000 fmol/mL.

Example 10

Plasma Renin Activity Calculations for 3 Hours Incubation

The basic process of reducing data was performed for 3 hours incubation. The dilution of plasma and generation time were taken into account in determining the final PRA value for samples analyzed in Examples 3-9, above, according to the following calculation:

$$\frac{250\ uL\ \text{plasma} + 25\ uL\ \text{buffer}}{250\ uL\ \text{plasma}} * \frac{1}{3\ \text{hours}} = 0.367$$

The result from LCquan reported as ng/mL was then multiplied by 0.367 to give a corrected measurement for the PRA assay in ng per mL per hr. Though in this particular Example an additional correction was not necessary, if the sample had been diluted to bring the final result into the linear range of the assay, the final result would also have been multiplied by the degree of dilution.

Figure 6:
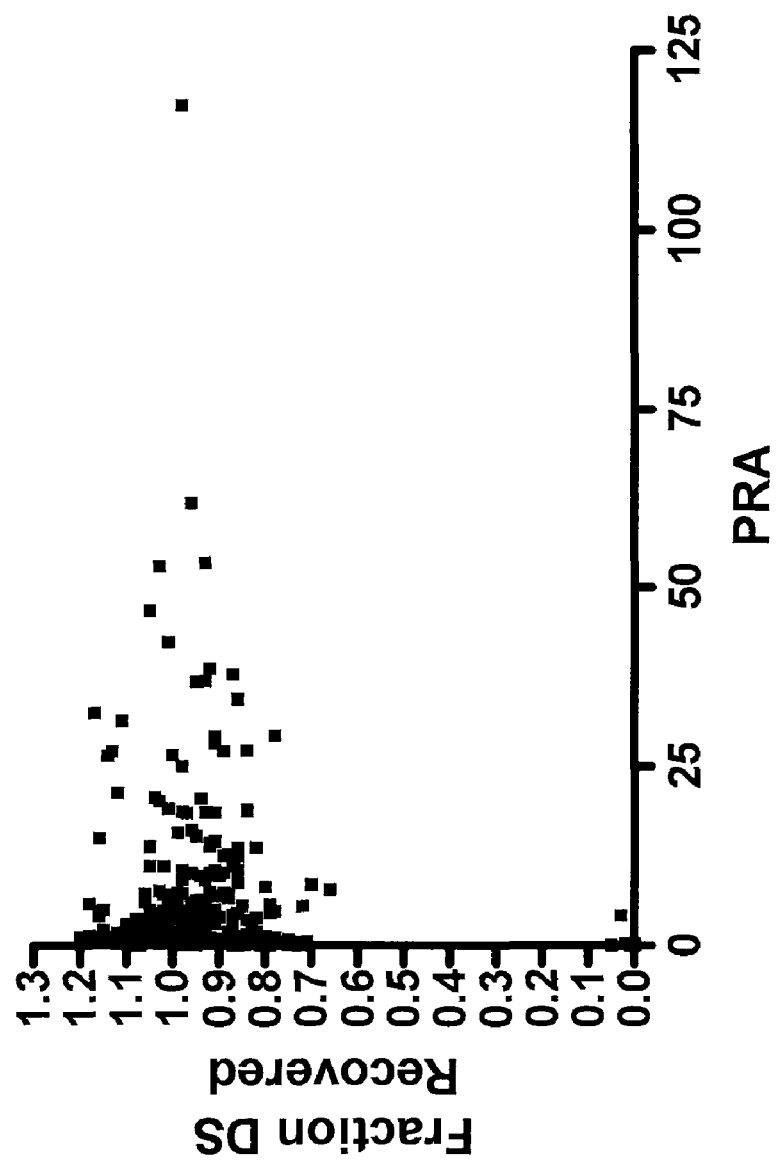
FIG. 6 shows the fraction of intact degradation standard observed as a function of the observed PRA in several patient samples.

FIG. 6 shows the fraction of intact degradation standard observed as a function of the observed PRA in several patient samples.

Example 11

Quantitation of Breakdown Products from Degradation Standard

As an alternative means to assess the degree of degradation of Ang1, generation of products from the breakdown of the degradation standard were measured. To do so, precursor ion scanning experiments utilized. The experiments were conducted by using isotope-labeled Ang1 peptides containing modified proline or histidine as the degradation standard. To monitor the accumulation of the degradation products, Q3 was set to select for immonium ions of isotope-labeled proline or histidine, while Q1 is scanned over m/z ranges that would be associated with N- or C-terminal degradation of the labeled Ang1 peptides. Table 5 contains a list of the m/z ratios of several of the breakdown product precursor ions that may be monitored to quantify accumulation of breakdown products. In the peptide sequences indicated in the table, isotopically-labeled histidines are indicated by "J".

Figure 7:
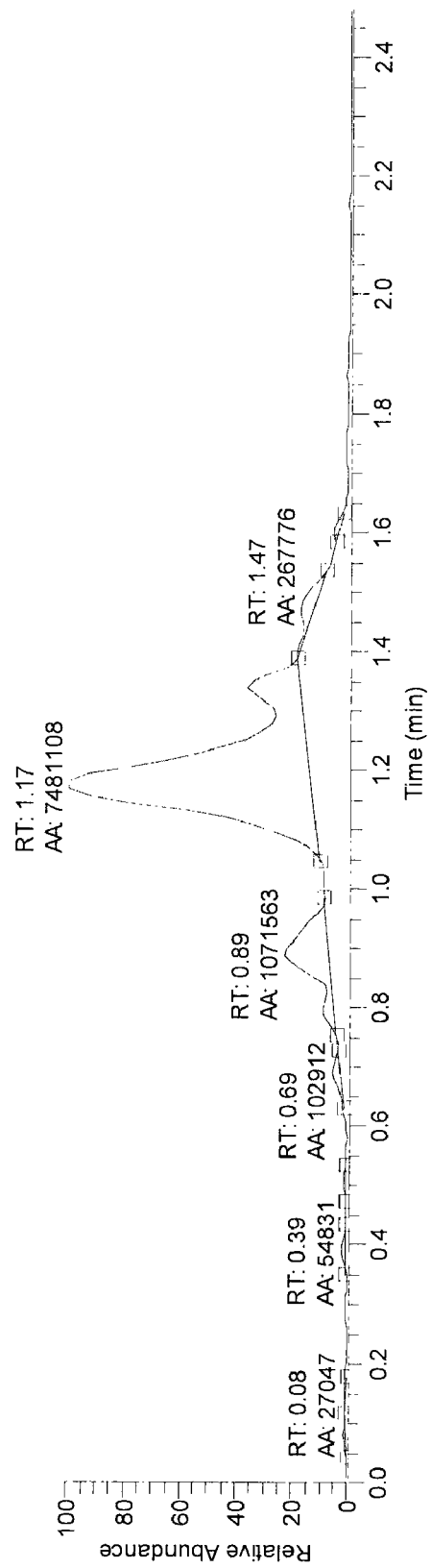
FIG. 7 shows a total ion chromatogram (with background subtracted) collected over retention times (RT) of 0.00 to about 2.49 minutes for precursor ion scanning across a m/z range of about 300.00 to about 650.00 for a highly degenerative sample.

FIG. 7 shows a total ion chromatogram collected over retention times (RT) of 0.00 to about 2.49 minutes for precursor ion scanning over a m/z range of about 300.00 to about 650.00. FIGS. 8-14 show spectra generated from precursor ion scanning over a m/z range of about 300.00 to about 650.00 at various retention times. These spectra show the relative abundance of several degradation standard breakdown product precursor ions indicated in Table 5.

Figure 8:
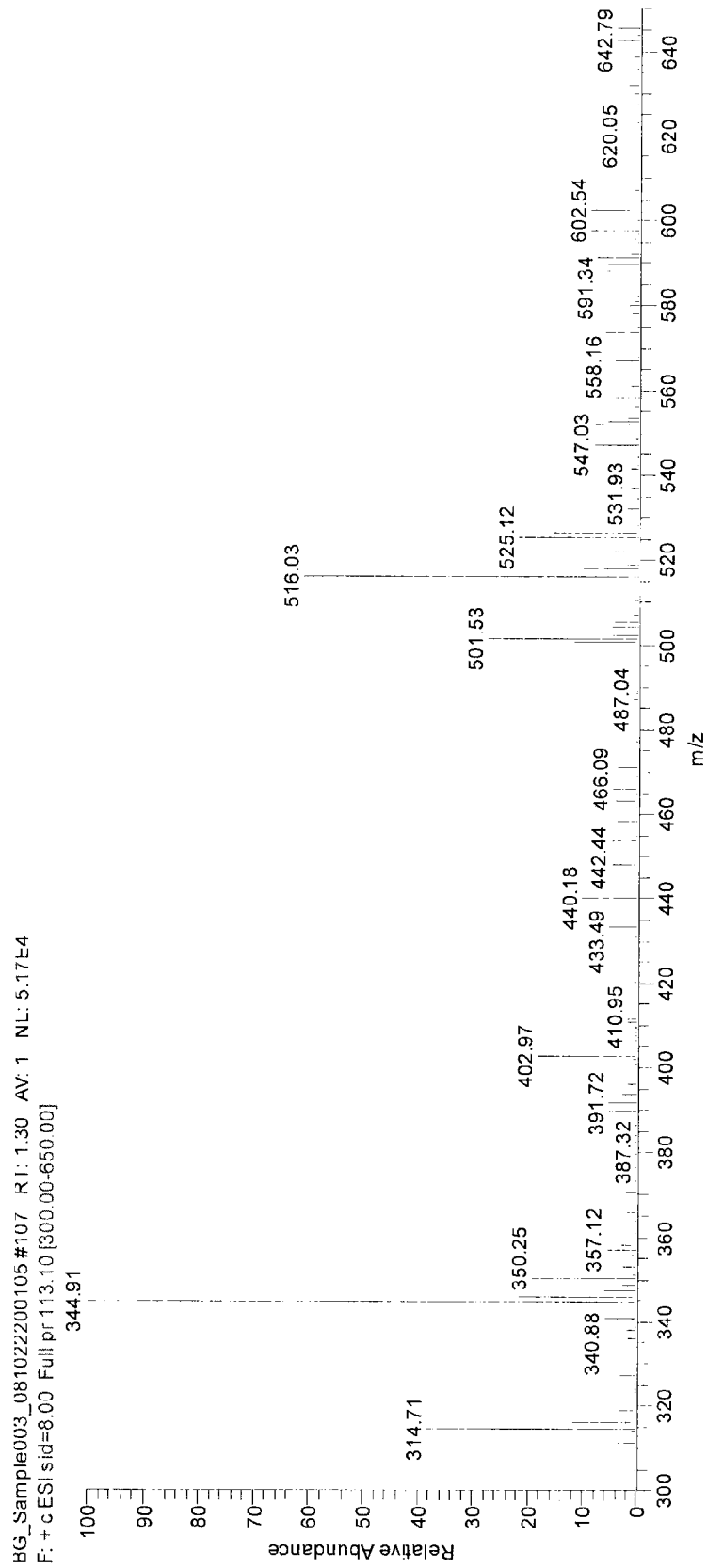
FIG. 8 shows precursor ion scanning spectra generated at RT of about 1.30 minutes across a m/z range of about 300.00 to about 650.00 for a highly degenerative sample.

For example, FIG. 8 (generated at RT of approximately 1.30 minutes) demonstrates m/z peaks at about 344.9±0.5 and about 516.0±0.5 which correspond to the breakdown product VYIJPFJL.

Figure 9:
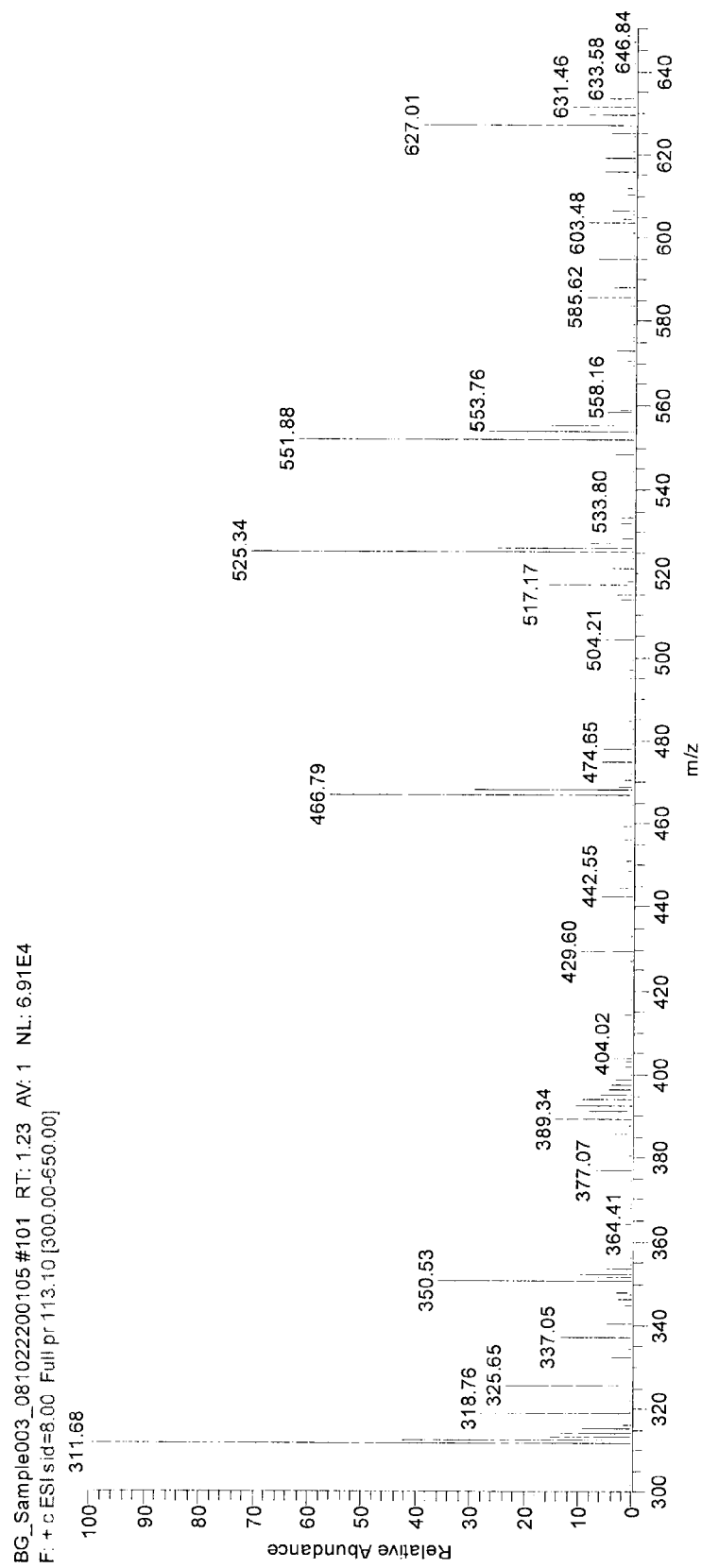
FIG. 9 shows precursor ion scanning spectra generated at RT of about 1.23 minutes across a m/z range of about 300.00 to about 650.00 for a highly degenerative sample.

FIG. 9 (generated at RT of approximately 1.23 minutes) demonstrates m/z peaks at about 311.7±0.5 and about 466.8±0.5 which correspond to the breakdown product YIJPFJL.

Figure 10:
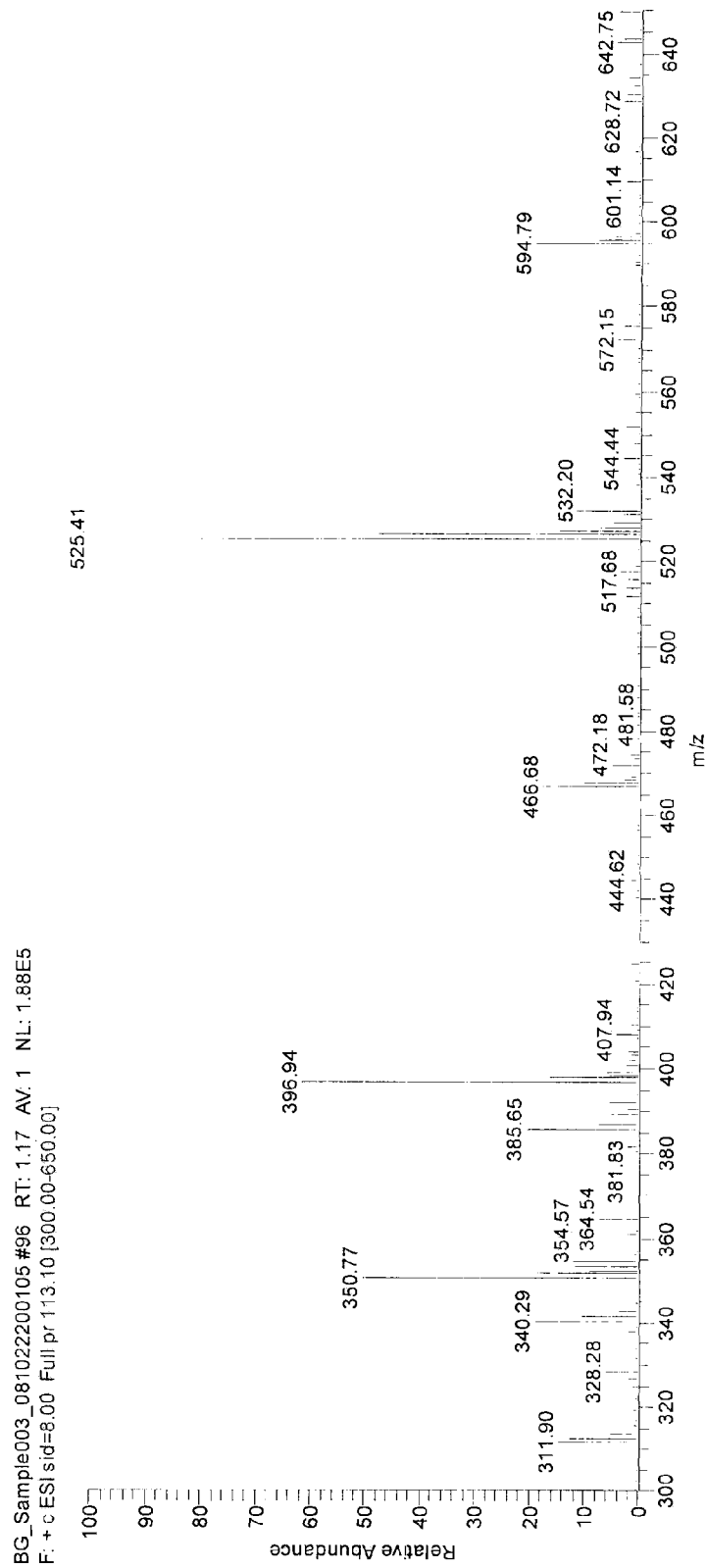
FIG. 10 shows precursor ion scanning spectra generated at RT of about 1.17 minutes across a m/z range of about 300.00 to about 650.00 for a highly degenerative sample.

FIG. 10 (generated at RT of approximately 1.17 minutes) demonstrates m/z peaks at about 350.8±0.5 and about 525.4±0.5 which correspond to the breakdown product DRVYIJPF, and m/z peaks at about 396.9±0.5 and about 594.8±0.5 which correspond to the breakdown product RVYIJPFJL.

Figure 11:
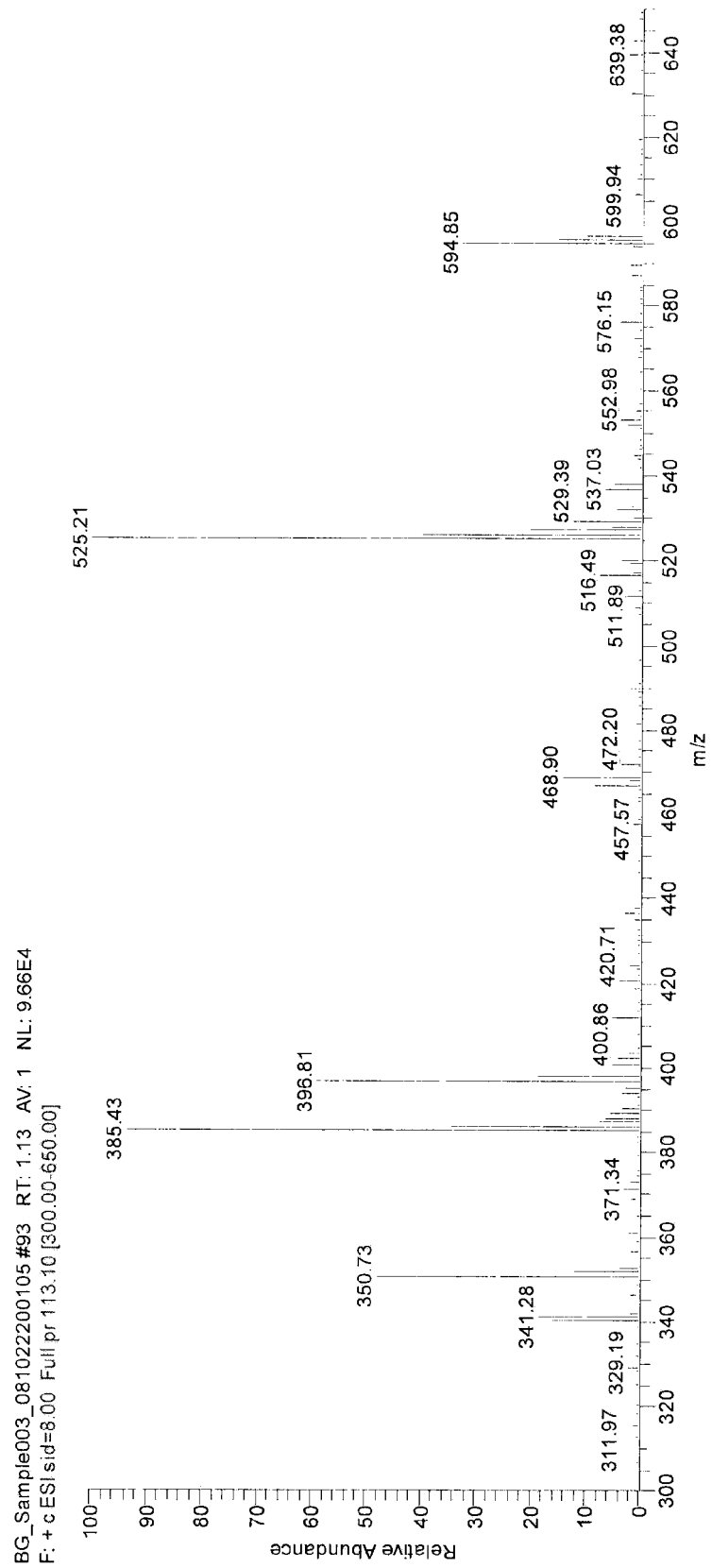
FIG. 11 shows precursor ion scanning spectra generated at RT of about 1.13 minutes across a m/z range of about 300.00 to about 650.00 for a highly degenerative sample.

FIG. 11 (generated at RT of approximately 1.13 minutes) demonstrates m/z peaks at about 350.7±0.5 and about 525.2±0.5 which correspond to the breakdown product DRVYIJPF, a m/z peak at about 385.4±0.5 which correspond to the breakdown product IJPFJL, and m/z peaks at about 396.8±0.5 and about 594.9±0.5 which correspond to the breakdown product DRVYIJPFJ.

Figure 12:
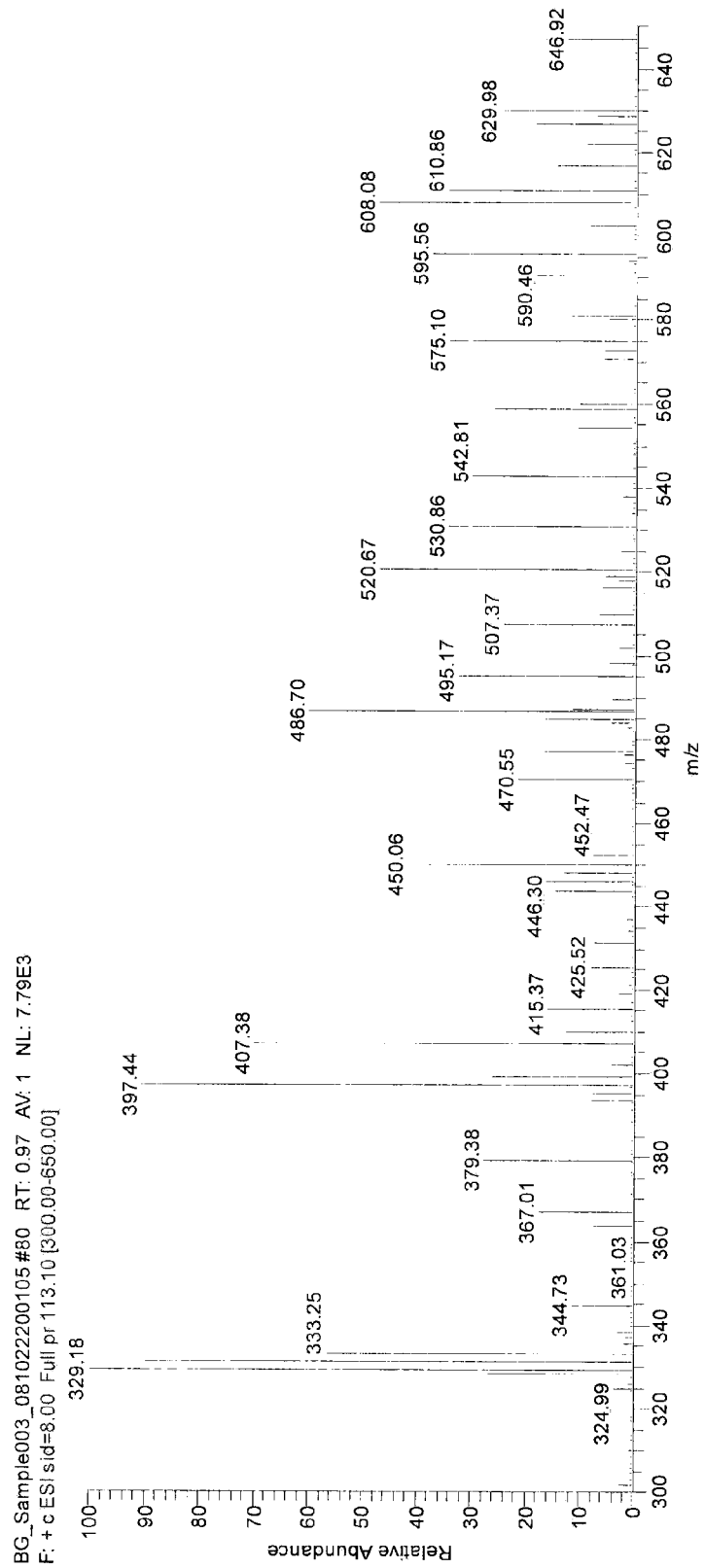
FIG. 12 shows precursor ion scanning, spectra generated at RT of about 0.97 minutes across a m/z range of about 300.00 to about 650.00 for a highly degenerative sample.

FIG. 12 (generated at RT of approximately 0.97 minutes) demonstrates m/z peaks at about 397.4±0.5 and about 595.6±0.5 which correspond to the breakdown product DRVYIJPFJ.

Figure 13:
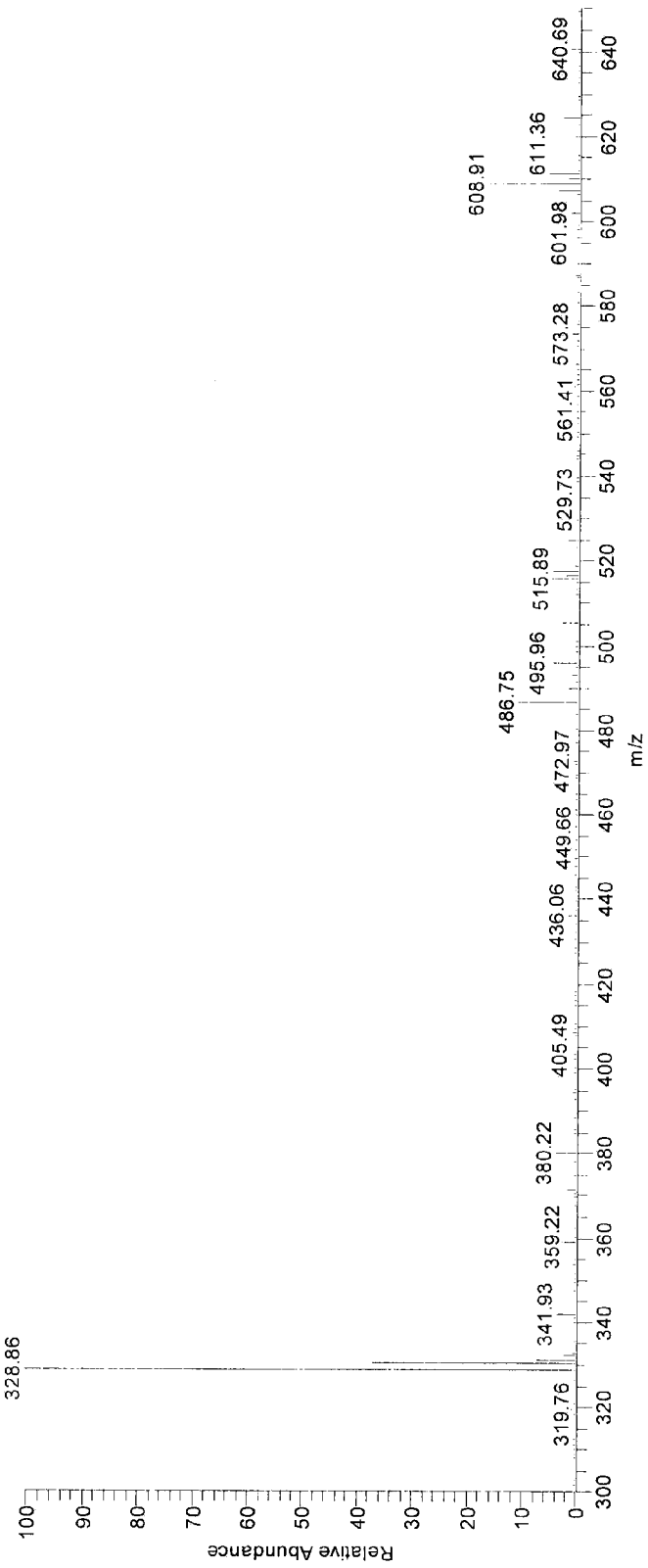
FIG. 13 shows precursor ion scanning spectra generated at RT of about 0.89 minutes across a m/z range of about 300.00 to about 650.00 for a highly degenerative sample.

FIG. 13 (generated at RT of approximately 0.89 minutes) demonstrates a m/z peak at about 328.9±0.5 which corresponds to the breakdown product JPFJL.

Figure 14:
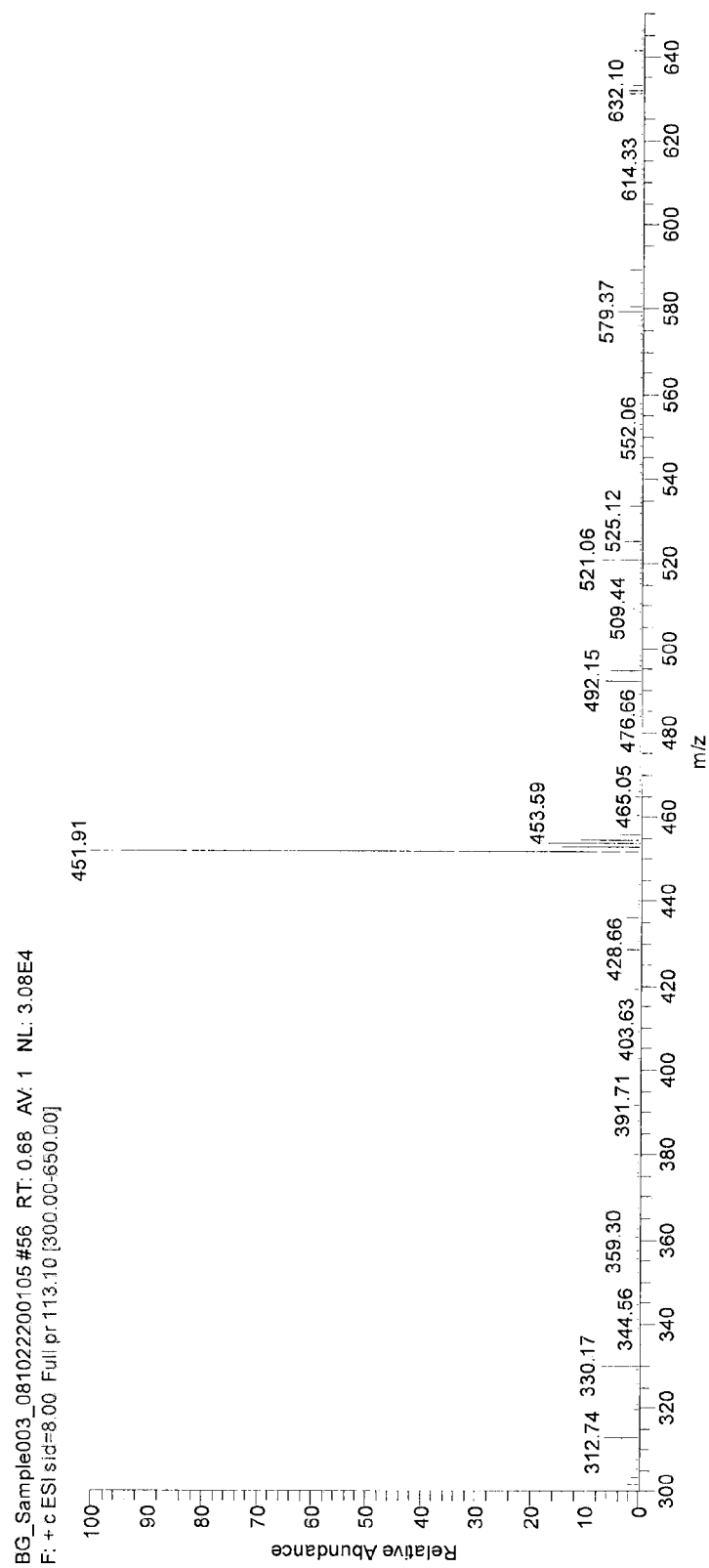
FIG. 14 shows precursor ion scanning spectra generated at RT of about 0.68 minutes across a m/z range of about 300.00 to about 650.00 for a highly degenerative sample.

FIG. 14 (generated at RT of approximately 0.68 minutes) demonstrates a m/z peak at about 451.9±0.5 which corresponds to the breakdown product DRVYIJP.

TABLE 5

M/Z ratios for various breakdown products of the degradation standard

| Peptide | Degradation Standard Breakdown Product Precursor Ions (m/z ± 0.5) | | | |
|---|---|---|---|---|
| | 1+ | 2+ | 3+ | 4+ |
| DRVYIJPFJL | 1302.7 | 651.8 | 434.9 | 326.4 |
| DRVYIJPFJ | 1189.6 | 595.3 | 397.2 | |
| RVYIJPFJL | 1187.7 | 594.3 | 396.5 | |
| RVYIJPFJ | | 537.8 | 358.9 | |
| DRVYIJPF | 1049.6 | 525.2 | 350.5 | |
| VYIJPFJL | 1031.6 | 516.0 | 344.5 | |
| RVYIJPF | | 467.8 | 312.2 | |
| YIJPFJL | 932.5 | 466.7 | 311.5 | |
| VYIJPFJ | | 459.8 | 306.8 | |
| DRVYIJP | 902.5 | 451.7 | 301.5 | |
| DRVYIJ | 805.4 | 403.2 | | |
| RVYIJP | | 394.2 | | |
| VYIJPF | | 389.7 | | |
| IJPFJL | 769.4 | 385.2 | | |
| JPFJL | 656.4 | 328.7 | | |
| PFJL | 516.3 | | | |

Example 12

Identification of Patient Sub-Population with High Degradation

A number of samples analyzed for the PRA according to methods outlined in the above Examples exhibited substantial loss (more than about 40% loss) of the degradation standard during incubation. If fact, a significant number of patient samples exhibited complete loss of the degradation standard during degradation. Experiments were conducted on several of these samples (n=371) to define a subpopulation of patients where observed low PRA is actually due to high levels of Ang1 degradation during incubation, rather than low renin activity.

The samples selected for analysis were specifically selected for further study based on previous PRA values determined by RIA with the intention of sampling a large number of patients with low PRA values (>0.65 ng/mL/hr). Patient samples were separated into 4 categories based on PRA values determined by RIA and LC-MS/MS: Group 1 with PRA values between <0.1-0.4 ng/m/hr (n=63); Group 2 with PRA values between 0.4-0.7 ng/m/hr (n=50); Group 3 with PRA values between 0.7-3.0 ng/m/hr (n=108); and Group 4 with PRA values of >3.0 ng/m/hr (150).

Of the samples in Group 1, eight samples exhibited a complete loss of degradation standard after three hours of incubation. Thus, the very low PRA values measured in about 12% (8 out of 63) of samples in Group 1 may result from high Ang1 degradation, rather than from a true lack of renin activity. However, the overall frequency of these highly degrading samples in the entire sample population is low (approximately 2%).

FIG. 14 shows the fraction degradation standard recovered intact as a function of PRA for The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for measuring the amount of angiotensin 1 in a sample, said method comprising:
    (a) incubating the sample under conditions suitable for the generation of angiotensin 1 by renin in the sample;
    (b) purifying angiotensin 1 in said sample by solid phase extraction;
    (c) ionizing the purified angiotensin 1 from said sample to produce one or more ions detectable by mass spectrometry;
    (d) detecting the amount of the angiotensin 1 ion(s) by mass spectrometry; and
    (e) using the amount of ion(s) detected to measure the amount of angiotensin 1 in said sample.

2. The method of claim 1, wherein said method has a limit of quantitation less than or equal to 0.1 ng/mL.

3. The method of claim 1, wherein said angiotensin 1 ions comprise one or more ions selected from the group consisting of ions with a mass/charge ratio of 433.0 ±0.5, 619.5 ±0.5, 647.4 ±0.5 and 1297 ±0.5.

4. The method of claim 1, wherein said ionizing comprises generating a precursor ion with a mass/charge ratio of 433.0 ±0.5, and generating one or more fragment ions selected from the group consisting of ions with a mass/charge ratio of 619.5 ±0.5 and 647.4 ±0.5.

5. The method of claim 1, wherein the amount of the angiotensin 1 ion is related to the presence or amount of angiotensin 1 in the sample by comparison to an internal standard.

6. The method of claim 1, wherein said incubation in step (a) comprises incubation in the presence of a water stable protease inhibitor that is not effective against renin.

7. The method of claim 6, wherein said water stable protease inhibitor is aminoethylbenzylsulfonyl fluoride.

8. The method of claim 1, further comprising measuring the degree of degradation of angiotensin 1 in the sample by adding a degradation standard to the sample prior to incubation and measuring the amount of degradation standard remaining after incubation.

9. The method of claim 1, further comprising measuring the degree of degradation of angiotensin 1 in the sample by adding a degradation standard to the sample prior to incubation and measuring the amount of breakdown products from degradation of the degradation standard in the sample after incubation.

10. A method for measuring renin activity in a sample, said method comprising,
    (a) incubating the sample under conditions suitable for the generation of angiotensin 1 by renin in the sample;
    (b) purifying angiotensin 1 by solid phase extraction;
    (c) ionizing the purified angiotensin 1 from said sample to produce one or more ions detectable by mass spectrometry;
    (d) detecting the amount of the angiotensin 1 ion(s) by mass spectrometry;
    (e) using the amount of ion(s) detected to measure the amount of angiotensin 1 in said sample; and
    (f) using the amount of angiotensin 1 measured in said sample to calculate renin activity in the sample.

11. The method of claim 10, wherein said method has a limit of quantitation less than or equal to 0.1 ng/mL.

12. The method of claim 10, wherein said angiotensin 1 ions comprise one or more ions selected from the group consisting of ions with a mass/charge ratio of 433.0 ±0.5, 619.5 ±0.5, 647.4 ±0.5 and 1297 ±0.5.

13. The method of claim 10, wherein said ionizing comprises generating a precursor ion with a mass/charge ratio of 433.0 ±0.5, and generating one or more fragment ions selected from the group consisting of ions with a mass/charge ratio of 619.5 ±0.5 or 647.4 ±0.5.

14. The method of claim 10, wherein said incubation in step (a) comprises incubation in the presence of a water stable protease inhibitor that is not effective against renin.

15. The method of claim 14, wherein said water stable protease inhibitor is aminoethylbenzylsulfonyl fluoride.

16. The method of claim 10, wherein the presence or amount of the angiotensin 1 ion is related to the presence or amount of angiotensin 1 in the sample by comparison to an internal standard.

17. The method of claim 10, further comprising measuring the degree of degradation of angiotensin 1 in the sample by adding a degradation standard to the sample prior to incubation and measuring the amount of degradation standard remaining after incubation.

18. The method of claim 10, further comprising measuring the degree of degradation of angiotensin 1 in the sample by adding a degradation standard to the sample prior to incubation and measuring the amount of breakdown products from degradation of the degradation standard in the sample after incubation.

19. A method for determining whether a patient exhibiting low plasma renin activity levels as determined by the method of claim 10 is a member of a subpopulation with high natural degradation of angiotensin 1, said method comprising: measuring the degree of degradation of angiotensin 1 in the sample by adding a degradation standard to the sample prior to incubation and measuring the amount of degradation standard remaining after incubation.

20. A method for measuring renin activity in a sample, said method comprising,
(a) incubating the sample premixed with a water stable protease inhibitor that is not effective against renin under conditions suitable for the generation of angiotensin 1 by renin in the sample;
(b) ionizing the angiotensin 1 from said sample to produce one or more ions detectable by mass spectrometry;
(c) detecting the amount of the angiotensin 1 ion(s) by mass spectrometry;
(d) using the amount of ion(s) detected to measure the amount of angiotensin 1 in said sample; and
(e) using the amount of angiotensin 1 measured in said sample to calculate renin activity in the sample.

21. The method of claim 20, wherein said method has a limit of quantitation less than or equal to 0.1 ng/mL.

22. The method of claim 20, wherein said angiotensin 1 ions comprise one or more ions selected from the group consisting of ions with a mass/charge ratio of 433.0 ±0.5, 619.5 ±0.5, 647.4 ±0.5 and 1297 ±0.5.

23. The method of claim 20, wherein said ionizing comprises generating a precursor ion with a mass/charge ratio of 433.0 ±0.5, and generating one or more fragment ions selected from the group consisting of ions with a mass/charge ratio of 619.5 ±0.5 or 647.4 ±0.5.

24. The method of claim 20, wherein said water stable protease inhibitor is aminoethylbenzylsulfonyl fluoride.

25. The method of claim 20, wherein the presence or amount of the angiotensin 1 ion is related to the presence or amount of angiotensin 1 in the sample by comparison to an internal standard.

26. The method of claim 20, further comprising measuring the degree of degradation of angiotensin 1 in the sample by adding a degradation standard to the sample prior to incubation and measuring the amount of degradation standard remaining after incubation.

27. The method of claim 20, further comprising measuring the degree of degradation of angiotensin 1 in the sample by adding a degradation standard to the sample prior to incubation and measuring the amount of breakdown products from degradation of the degradation standard in the sample after incubation.

28. A method for determining whether a patient exhibiting low plasma renin activity levels as determined by the method of claim 20 is a member of a subpopulation with high natural degradation of angiotensin 1 , said method comprising: measuring the degree of degradation of angiotensin 1 in the sample by adding a degradation standard to the sample prior to incubation and measuring the amount of degradation standard remaining after incubation.

* * * * *